(12) United States Patent
Kester et al.

(10) Patent No.: US 6,608,218 B2
(45) Date of Patent: Aug. 19, 2003

(54) α-ACYL- AND α-HETEROATOM-SUBSTITUTED BENZENE ACETAMIDE GLUCOKINASE ACTIVATORS

(75) Inventors: Robert Francis Kester, West Orange, NJ (US); Ramakanth Sarabu, Pine Brook, NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 10/179,717

(22) Filed: Jun. 25, 2002

(65) Prior Publication Data
US 2002/0198200 A1 Dec. 26, 2002

Related U.S. Application Data

(62) Division of application No. 09/905,152, filed on Jul. 13, 2001.
(60) Provisional application No. 60/219,872, filed on Jul. 20, 2000.

(51) Int. Cl.$^7$ .............................................. C07D 309/02
(52) U.S. Cl. ...................................... 549/419; 564/155

(58) Field of Search ......................... 564/155; 546/291; 549/419

(56) References Cited

U.S. PATENT DOCUMENTS 3,776,917 A    12/1973    Mann et al.

FOREIGN PATENT DOCUMENTS

| JP | 55064592 | 5/1980 |
|---|---|---|
| WO | WO 00/58293 | 10/2000 |

OTHER PUBLICATIONS

Teijin Ltd., *Chemical Abstracts*, JP 55 064592 (1980).
Asthana T. et al., *Chemical Abstracts*, 74, No. 21, pp. 256 (1971).
Asthana T. et al, *Chemical Abstracts, Indian J. Chem.*, 8 No. 12, pp. 1086–1095 (1970).

*Primary Examiner*—Zinna Northington Davis
(74) *Attorney, Agent, or Firm*—George W. Johnston; John P. Parise

(57) ABSTRACT

Substituted benzene acetamide compounds and pharmaceutically acceptable salts thereof are useful as glucokinase activators.

15 Claims, No Drawings

α-ACYL- AND α-HETEROATOM-SUBSTITUTED BENZENE ACETAMIDE GLUCOKINASE ACTIVATORS

CROSS-REFERENCE TO RELATED APPLICATIONS

This application is a divisional of U.S. patent application Ser. No. 09/905,152, filed Jul. 13, 2001, which claims priority of U.S. Provisional Patent Application No. 60/219,872, filed Jul. 20, 2000.

BACKGROUND OF THE INVENTION

This application is relevant to U.S. Ser. No. 09/526,143, filed Mar. 15, 2000 (now U.S. Pat. No. 6,320,050) and U.S. Ser. No. 09/532,506, filed Mar. 21, 2000.

Glucokinase (GK) is one of four hexokinases found in mammals [Colowick, S. P., in *The Enzymes*, Vol. 9 (P. Boyer, ed.) Academic Press, New York, N.Y., pages 1–48, 1973]. The hexokinases catalyze the first step in the metabolism of glucose, i.e., the conversion of glucose to glucose-6-phosphate. Glucokinase has a limited cellular distribution, being found principally in pancreatic β-cells and liver parenchymal cells. In addition, GK is a rate-controlling enzyme for glucose metabolism in these two cell types that are known to play critical roles in whole-body glucose homeostasis [Chipkin, S. R., Kelly, K. L., and Ruderman, N. B. in *Joslin's Diabetes* (C. R. Khan and G. C. Wier, eds.), Lea and Febiger, Philadelphia, Pa., pages 97–115, 1994]. The concentration of glucose at which GK demonstrates half-maximal activity is approximately 8 mM. The other three hexokinases are saturated with glucose at much lower concentrations (<1 mM). Therefore, the flux of glucose through the GK pathway rises as the concentration of glucose in the blood increases from fasting (5 mM) to postprandial (≈10–15 mM) levels following a carbohydrate-containing meal [Printz, R. G., Magnuson, M. A., and Granner, D. K. in *Ann. Rev. Nutrition* Vol. 13 (R. E. Olson, D. M. Bier, and D. B. McCormick, eds.), Annual Review, Inc., Palo Alto, Calif., pages 463–496, 1993]. These findings contributed over a decade ago to the hypothesis that GK functions as a glucose sensor in β-cells and hepatocytes (Meglasson, M. D. and Matschinsky, F. M. *Amer. J. Physiol.* 246, E1–E13, 1984). In recent years, studies in transgenic animals have confirmed that GK does indeed play a critical role in whole-body glucose homeostasis. Animals that do not express GK die within days of birth with severe diabetes while animals overexpressing GK have improved glucose tolerance (Grupe, A., Hultgren, B., Ryan, A. et al., *Cell* 83, 69–78, 1995; Ferrie, T., Riu, E., Bosch, F. et al., *FASEB J,* 10, 1213–1218, 1996). An increase in glucose exposure is coupled through GK in β-cells to increased insulin secretion and in hepatocytes to increased glycogen deposition and perhaps decreased glucose production.

The finding that type II maturity-onset diabetes of the young (MODY-2) is caused by loss of function mutations in the GK gene suggests that GK also functions as a glucose sensor in humans (Liang, Y., Kesavan, P., Wang, L. et al., *Biochem. J.* 309, 167–173, 1995). Additional evidence supporting an important role for GK in the regulation of glucose metabolism in humans was provided by the identification of patients that express a mutant form of GK with increased enzymatic activity. These patients exhibit a fasting hypoglycemia associated with an inappropriately elevated level of plasma insulin (Glaser, B., Kesavan, P., Heyman, M. et al., *New England J. Med.* 338, 226–230, 1998). While mutations of the GK gene are not found in the majority of patients with type II diabetes, compounds that activate GK and, thereby, increase the sensitivity of the GK sensor system will still be useful in the treatment of the hyperglycemia characteristic of all type II diabetes. Glucokinase activators will increase the flux of glucose metabolism in β-cells and hepatocytes, which will be coupled to increased insulin secretion. Such agents would be useful for treating type II diabetes.

SUMMARY OF THE INVENTION

This invention provides an amide selected from the group consisting of a compound of the formula:

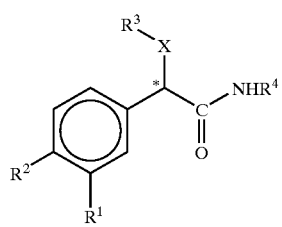

I wherein $R^1$ and $R^2$ are independently hydrogen, halo, cyano, nitro, loweralkylthio, perfluoro lower alkylthio, lower alkyl sulfonyl, or perfluoro-lower alkyl sulfonyl, $R^3$ is lower alkyl having from 2 to 4 carbon atoms or a 5 to 7-membered ring which is cycloalkyl, cycloalkenyl, or heterocycloalkyl having one heteroatom selected from oxygen and sulfur, $R^4$ is —C(O)NHR$^5$, or is $R^6$, which is an unsubstituted or mono-substituted five- or six-membered heteroaromatic ring connected by a ring carbon atom to the amide group shown, which five- or six-membered heteroaromatic ring contains from 1 to 3 heteroatoms selected from sulfur, oxygen or nitrogen, with one heteroatom being nitrogen which is adjacent to the connecting ring carbon atom; with said mono-substituted heteroaromatic ring being monosubstituted at a position on a ring carbon atom other than adjacent to said connecting carbon atom with a substituent selected from the group consisting of lower alkyl, halo, nitro, cyano, —(CH$_2$)$_n$—OR$^9$, —(CH$_2$)$_n$—C(O)—OR$^{10}$, —(CH$_2$)$_n$—C(O)—NH—R$^{11}$, —C(O)—C(O)—OR$^{12}$, —(CH$_2$)$_n$—NHR$^{13}$; n is 0, 1, 2, 3 or 4; $R^7$, $R^8$, $R^9$, $R^{10}$, $R^{11}$, $R^{12}$, $R^{13}$ are independently hydrogen or lower alkyl, $R^5$ is hydrogen, lower alky, lower alkenyl, hydroxy lower alkyl, halo lower alkyl, —(CH$_2$)$_n$—C(O)—OR$^7$, —C(O)—(CH$_2$)$_n$—C(O)—OR$^8$, X is oxygen, sulfur, sulfonyl, or carbonyl; the * indicates an asymmetric carbon atom; and its pharmaceutically acceptable salts.

Preferably, the compound of formula I is in the "R" configuration at the asymmetric carbon, shown except in the case where X is carbonyl (C=O), when the preferred enantiomer is "S".

The compounds of formula I have been found to activate glucokinase. Glucokinase activators are useful in the treatment of type II diabetes.

DETAILED DESCRIPTION OF THE INVENTION

The subject invention will now be described in terms of its preferred embodiments. These embodiments are set forth to aid in understanding the invention but are not to be construed as limiting.

In one embodiment, this invention provides amides of formula I, comprising compounds of formulae II and III as follows:

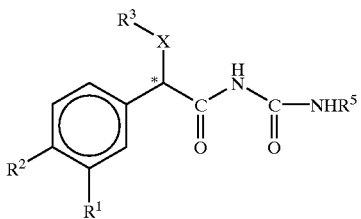

(II)

wherein $R^1$ and $R^2$ are independently hydrogen, halo, cyano, nitro, lower alkylthio, perfluoro lower alkylthio, lower alkyl sulfonyl, or perfluoro-lower alkyl sulfonyl, (preferably hydrogen, halo, lower alkyl sulfonyl, or perfluoro lower alkyl sulfonyl) $R^3$ is a 5 to 7-membered ring which is cycloalkyl, cycloalkenyl, or heterocycloalkyl having one heteroatom selected from oxygen and sulfur, $R^5$ is lower alkyl, X is oxygen, sulfur, sulfonyl or carbonyl, the * indicates an asymmetric carbon atom and

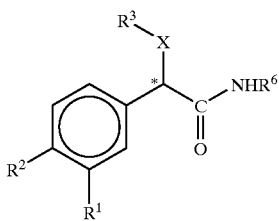

(III)

wherein $R^1$ and $R^2$ are independently hydrogen, halo, cyano, nitro, lower alkylthio, perfluoro lower alkyl thio, lower alkyl sulfonyl, or perfluoro-lower alkyl sulfonyl, (preferably hydrogen, halo, lower alkyl sulfonyl, or perfluoro lower alkyl sulfonyl) $R^3$ is a 5 to 7-membered ring which is cycloalkyl, cycloalkenyl, or heterocycloalkyl having one heteroatom selected from oxygen and sulfur, $R^6$ is an unsubstituted five- or six-membered heteroaromatic ring connected by a ring carbon atom to the amide group shown, which five- or six-membered heteroaromatic ring contains from 1 to 3 heteroatoms selected from sulfur, oxygen or nitrogen, with one heteroatom being nitrogen which is adjacent to the connecting ring carbon atom, X is oxygen, sulfur, sulfonyl or carbonyl, and the * indicates an asymmetric carbon atom Preferably, the compounds of formulae II and III are in the "R" configuration at the asymmetric carbon shown except in the case where X is carbonyl (C=O), when the preferred enantiomer is "S". The pharmaceutically acceptable salts of each amide of this invention are compounds of this invention.

In preferred amides of formula II, $R^1$ and $R^2$ are independently halo or lower alkyl sulfonyl, $R^3$ is a 5 to 7-membered ring which is cyclopentyl, cyclohexyl, cyclohexenyl, or heterocycloalkyl having one heteroatom selected from oxygen and sulfur (preferably oxygen) (Compound A).

In certain amides of Compound A, $R^5$ is methyl, and X is oxygen. More preferably $R^1$ and $R^2$ are independently chloro or methyl sulfonyl (which means $R^1$ and $R^2$ may each be chloro or methyl sulfonyl, or one is chloro while the other is methyl sulfonyl) (compound A-1). Examples of such compounds where $R^1$ and $R^2$ are chloro are 1-[cyclopentyloxy-(3,4-dichloro-phenyl)-acetyl]-3-methyl-urea, 1-[cyclohexyloxy-(3,4-dichloro-phenyl)-acetyl]-3-methyl-urea, 1-[(cyclohex-2-enyloxy)-(3,4-dichloro-phenyl)-acetyl]-3-methyl-urea and

[1-[(3,4-dichloro-phenyl)-(tetrahydro-pyran-4-yloxy)-acetyl]-3-methyl-urea.

Examples of the amides of Compound A-1 where $R^1$ is chloro and $R^2$ is methyl sulfonyl are 1-[(3-chloro-4-methanesulfonyl-phenyl)-cyclopentyloxy-acetyl]-3-methyl-urea and 1-[(3-chloro-4-methanesulfonyl-phenyl)-(cyclohex-2-enyloxy)-acetyl]-3-methyl-urea.

In preferred amides of formula III, $R^1$ and $R^2$ are independently halo or lower alkyl sulfonyl, $R^3$ is a 5 to 7-membered ring which is cyclopentyl, cyclohexyl, cyclohexenyl, or heterocycloalkyl having one heteroatom selected from oxygen and sulfur (preferably oxygen) (Compound B). Preferably $R^6$ is thiazolyl or pyridinyl, and $R^1$ and $R^2$ are independently chloro or methyl sulfonyl (Compound B-1).

In certain amides of Compound B-1, it is preferred that X is oxygen, especially when $R^1$ and $R^2$ are chloro and $R^6$ is thiazolyl or pyridinyl. Examples of such compounds where $R^6$ is thiazolyl are:

2-(3,4-dichloro-phenyl)-2-(tetrahydro-pyran-4-yloxy)-N-thiazol-2-yl-acetamide,

2-Cyclopentyloxy-2-(3,4-dichloro-phenyl)-N-thiazol-2-yl-acetamide,

2-Cyclohexyloxy-2-(3,4-dichloro-phenyl)-N-thiazol-2-yl-acetamide, and 2-(Cyclohex-2-enyloxy)-2-(3,4-dichloro-phenyl)-N-thiazol-2-yl-acetamide.

An example of such compounds where $R^6$ is pyridinyl is 2-Cyclopentyloxy-2-(3,4-dichloro-phenyl)-N-pyridin-2-yl-acetamide.

In another amide of Compound B-1 where X is oxygen, $R^1$ is chloro and $R^2$ is methyl sulfonyl. Examples of such compounds are:

2-(3-chloro-4-methanesulfonyl-phenyl)-2-cyclopentyloxy-N-thiazol-2-yl-acetamide and 2-(3-chloro-4-methanesulfonyl-phenyl)-2-(cyclohex-2-enyloxy-N-(4,5-dihydro-thiazol-2-yl-acetamide.

In yet another amide of Compound B-1, X is sulfur, sulfonyl or carbonyl, $R^1$ and $R^2$ are chloro, and $R^3$ is cyclopentyl. Examples of such compounds are:

3-Cyclopentyl-2-(3,4-dichloro-phenyl)-3-oxo-N-thiazol-2-yl-propionamide,

2-Cyclopentanesulfonyl-2-(3,4-dichloro-phenyl)-N-thiazol-2-yl-acetamide and

2-Cyclopentylsulfanyl-2-(3,4-dichloro-phenyl)-N-thiazol-2-yl-acetamide.

For each compound described above, each variable which is specifically indicated may be combined with any other variable of formula I or may be combined with any one or more specifically indicated variable.

In the compound of formula I, the * indicates the asymmetric carbon. The compound of formula I may be present either as a racemate or in the "R" configuration at except in the case where X is carbonyl (C=O), when the preferred enantiomer is "S". the asymmetric carbon shown. The "R" enantiomers are preferred, Where $R^3$ is asymmetric an additional chiral center at the ring carbon connected with X is generated. At this center the compounds of formula I may be present as a racemate or in the "R" or "S" configuration.

As used herein, the term "halogen" and the term "halo", unless otherwise stated, designate all four halogens, i.e. fluorine, chlorine, bromine and iodine. Preferred halogens are chlorine and bromine, most preferred is chlorine.

As used throughout this application, the term "lower alkyl" includes both straight chain and branched chain alkyl groups having from 1 to 7 carbon atoms, such as methyl, ethyl, propyl, isopropyl, preferably methyl. As used herein, "lower alkyl sulfonyl" means a lower alkyl group as defined above bound to the rest of the molecule through the sulfur atom in the sulfonyl group. Similarly "perfluoro-lower alkyl sulfonyl" means a perfluoro-lower alkyl group as defined above bound to the rest of the molecule through the sulfur atom in the sulfonyl group.

As used herein, "lower alkyl thio" means a lower alkyl group as defined above where a thio group is bound to the rest of the molecule. Similarly "perfluoro-lower alkyl thio" means a perfluoro-lower alkyl group as defined above where a thio group is bound to the rest of the molecule.

As used herein, "cycloalkyl" means a saturated hydrocarbon ring having from 3 to 10 carbon atoms, preferably from 5 to 7 carbon atoms. Preferred cycloalkyls are cyclopentyl and cyclohexyl. As used herein, "cycloalkenyl" means a cycloalkyl ring having from 3 to 10, and preferably from 5 to 7 carbon atoms, where one of the bonds between the ring carbons is unsaturated. As used herein, "heterocycloalkyl" means a saturated hydrocarbon ring having from 3 to 10 carbon atoms, preferably from 5 to 7 carbon atoms, and having a heteroatom which may be oxygen or sulfur. It is preferred to have a single heteroatom, preferably oxygen.

As used herein, the term "lower alkenyl" denotes an alkylene group having from 2 to 6 carbon atoms with a double bond located between any two adjacent carbons of the group. Preferred lower alkenyl groups are allyl and crotyl.

The variable X may be an oxygen or sulfur (i.e. —O— or —S—) or sulfonyl or carbonyl (i.e. $SO_2$ or C=O).

The heteroaromatic ring can be an unsubstituted or monosubstituted five- or six-membered heteroaromatic ring having from 1 to 3 heteroatoms selected from the group consisting of oxygen, nitrogen, or sulfur and connected by a ring carbon to the amide group shown. The heteroaromatic ring has at least one nitrogen atom adjacent to the connecting ring carbon atom and if present, the other heteroatoms can be sulfur, oxygen or nitrogen. Certain preferred rings contain a nitrogen atom adjacent to the connecting ring carbon and a second heteroatom adjacent to the connecting ring carbon or adjacent to said first heteroatom. The heteroaromatic rings are connected via a ring carbon atom to the amide group. The ring carbon atom of the heteroaromatic ring which is connected via the amide linkage cannot contain any substituent. Heteroaromatic rings include, for example, pyrazinyl, pyridazinyl, isoxazolyl, isothiazolyl, pyrazolyl, pyridinyl, pyrimidinyl, thiadiazolyl (preferably 1,3,4-, 1,2, 3-, 1,2,4-), triazinyl (preferably 1,3,5-, 1,2,4-), thiazolyl; oxazolyl, and imidazolyl. Preferred rings are thiazolyl for example 4 or 5-halothiazolyl, 4 or 5 lower alkyl thiazolyl, pyridinyl, and pyrimidinyl, for example 2-lower alkyl pyrimidinyl. Most preferred are thiazolyl or pyridinyl.

Preferable compounds in accordance with the present invention are compounds of above formula I, wherein $R^5$ is lower alkyl, preferably methyl. In one embodiment, preferable heteroaromaric ring $R^6$ is thiazolyl; in another embodiment, preferable heteroaromatic ring $R^6$ is pyridinyl. In one embodiment, preferable $R^1$ and $R^2$ are independently halo (preferably chloro) or lower alkyl sulfonyl (preferably methyl sulfonyl); in another embodiment, $R^1$ and $R^2$ are chloro; in still another embodiment, $R^1$ is chloro and $R^2$ is methyl sulfonyl. Preferable residue $R^3$ is cyclopentyl, cyclohexyl, cyclohexenyl, with cyclopentyl being preferred, or a six-membered heterocycloalkyl having one heteroatom selected from oxygen and sulfur, with oxygen being preferred. In one embodiment, X is oxygen; in another embodiment, X is sulfur, sulfonyl or carbonyl.

Most preferable compounds in accordance with the present invention are:

1-[cyclopentyloxy-(3,4-dichloro-phenyl)-acetyl]-3-methyl-urea,

1-[cyclohexyloxy-(3,4-dichloro-phenyl)-acetyl]-3-methyl-urea,

1-[(cyclohex-2-enyloxy)-(3,4-dichloro-phenyl)-acetyl]-3-methyl-urea,

[1-[(3,4-dichloro-phenyl)-(tetrahydro-pyran-4-yloxy)-acetyl]-3-methyl-urea,

1-[(3-chloro-4-methanesulfonyl-phenyl)-cyclopentyloxy-acetyl]-3-methyl-urea,

1-[(3-chloro-4-methanesulfonyl-phenyl)-(cyclohex-2-enyloxy)-acetyl]-3-methyl-urea, 2-(3,4-dichloro-phenyl)-2-(tetraydro-pyran-4-yloxy)-N-thiazol-2-yl-acetamide, 2-cyclopentyloxy-2-(3,4-dichloro-phenyl)-N-thiazol-2-yl-acetamide, 2-cyclohexyloxy-2-(3,4-dichloro-phenyl)-N-thiazol-2-yl-acetamide, 2-(cyclohex-2-enyloxy)-2-(3,4-dichloro-phenyl)-N-thiazol-2-yl-acetamide, 2-cyclopentyloxy-2-(3,4-dichloro-phenyl)-N-pyridin-2-yl-acetamide, 2-(3-chloro-4-methanesulfonyl-phenyl)-2-cyclopentyloxy-N-thiazol-2-yl-acetamide, 2-(3-chloro-4-methanesulfonyl-phenyl)-2-(cyclohex-2-enyloxy-N-(4,5-dihydro-thiazol-2-yl-acetamide, 3-cyclopentyl-2-(3,4-dichloro-phenyl)-3-oxo-N-thiazol-2-yl-propionaimide, 2-cyclopentanesulfonyl-2-(3,4-dichloro-phenyl)-N-thiazol-2-yl-acetamide and 2-cyclopentylsulfanyl-2-(3,4-dichloro-phenyl)-N-thiazol-0.2-yl-acetamide.

The term "pharmaceutically acceptable salts" as used herein include any salt with both inorganic or organic pharmaceutically acceptable acids such as hydrochloric acid, hydrobromic acid, nitric acid, sulfuric acid, phosphoric acid, citric acid, formic acid, maleic acid, acetic acid, succinic acid, tartaric acid, methanesulfonic acid, para-toluene sulfonic acid and the like. The term "pharmaceutically acceptable salts" also includes any pharmaceutically acceptable base salt such as amine salts, trialkyl amine salts and the like. Such salts can be formed quite readily by those skilled in the art using standard techniques. This invention includes the pharmaceutically acceptable salt of each compound of formula I.

The compound of formula I can be prepared by the following Reaction Schemes which follow.

During the course of the reactions, the various functional groups such as the free carboxylic acid or hydroxy groups will be protected via conventional hydrolyzable ester or ether protecting groups. As used herein the term "hydrolyzable ester or ether protecting groups" designates any ester or ether conventionally used for protecting carboxylic acids or alcohols which can be hydrolyzed to yield the respective hydroxyl or carboxyl group. Exemplary ester groups useful for the protection of a hydroxyl group are those in which the acyl moieties are derived from a lower alkanoic, aryl lower alkanoic, or lower alkane dicarboxcyclic acid. Among the activated acids which can be utilized to form such groups are acid anhydrides, acid halides, preferably acid chlorides or acid bromides derived from aryl or lower alkanoic acids. Example of anhydrides are anhydrides derived from mono-carboxylic acid such as acetic anhydride, benzoic acid anhydride, and lower alkane dicarboxcyclic acid anhydrides, e.g. succinic anhydride. Suitable ether protecting groups for alcohols are, for example, the tetrahydropyranyl ethers such as 4-methoxy-5,6-dihydroxy-2H-pyranyl ethers. Others are aroyl substituted methyl ethers such as benzyl or trityl ethers or α-lower alkoxy lower alkyl ethers, for example, methoxymethyl or allylic ethers or alkyl silylethers such as trimethylsilylether.

Exemplary ester groups useful for the protection of carboxylic acid groups are those derived from lower alkanols or substituted or unsubstituted benzyl alcohols. The choice of ester functions used is well known to those of ordinary skill in the art of organic chemistry. For example, the ester functions most readily cleaved under basic hydrolysis are those derived from lower primary alcohols such as methyl, ethyl, and the like. Ester functions derived from secondary or tertiary alcohols are more readily cleaved under acidic conditions, for example tertiary butyl or diphenylmethyl esters. Benzyl esters are particularly useful for the protection of carboxylic acid functions in compounds that are stable to the hydrogenolytic conditions that can be used to remove the protecting group.

The term "amino protecting group" designates any conventional amino protecting group which can be cleaved to yield the free amino group. The preferred protecting groups are the conventional amino protecting groups such as those utilized in peptide synthesis, particularly the carbamates. Particularly preferred amino protecting groups in this class are t-butoxycarbonyl (BOC), carbobenzyloxy (CBZ), and 9-fluorenylmethoxy-carbonyl (FMOC) moieties. Each of these protecting groups is readily removed under reaction conditions that do not affect the others. For example FMOC and CBZ protecting groups are stable to the acidic conditions used to remove BOC groups and other acid labile moieties. CBZ groups can be removed by hydrogenolysis in the presence of FMOC and BOC protecting groups, while the FMOC moiety is particularly labile in the presence of secondary cyclic amines, conditions under which BOC and CBZ groups are unaffected.

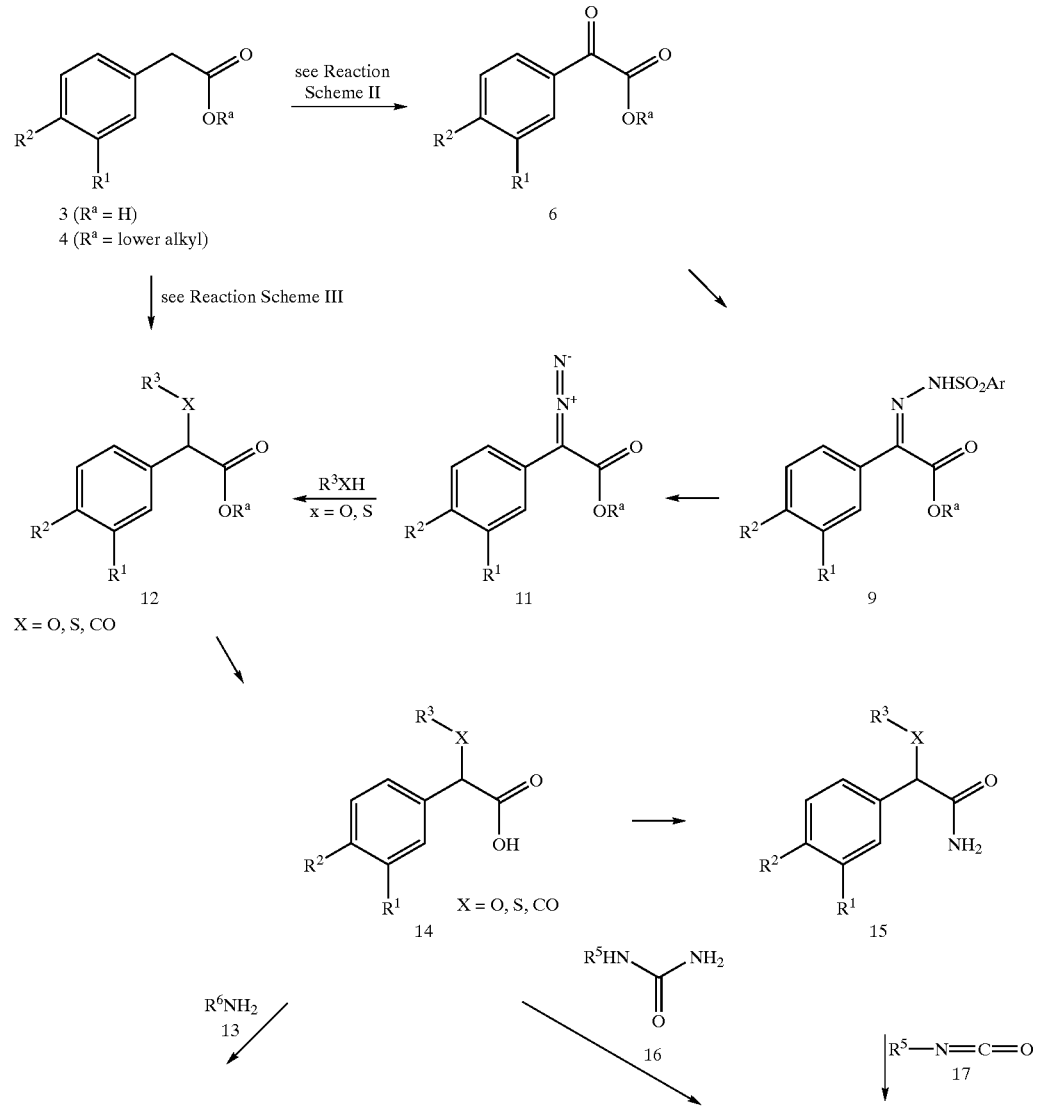

Reaction Scheme I

-continued
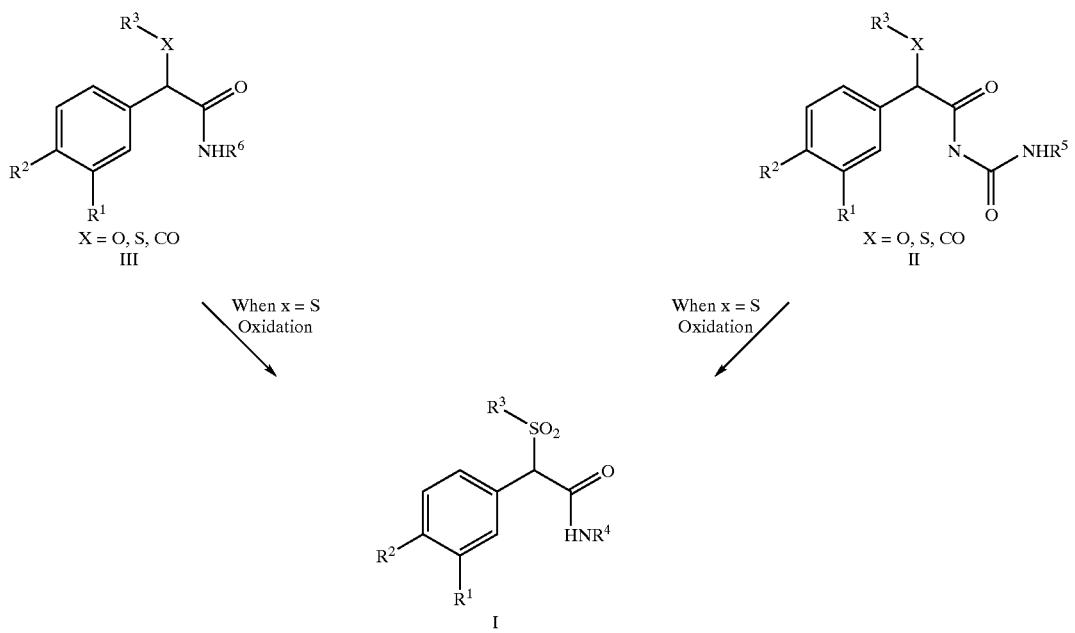
Reaction Scheme II
Methods to prepare Phenyl Pyruvates of Structure 6
Via α-hydroxyphenyl acetic acid
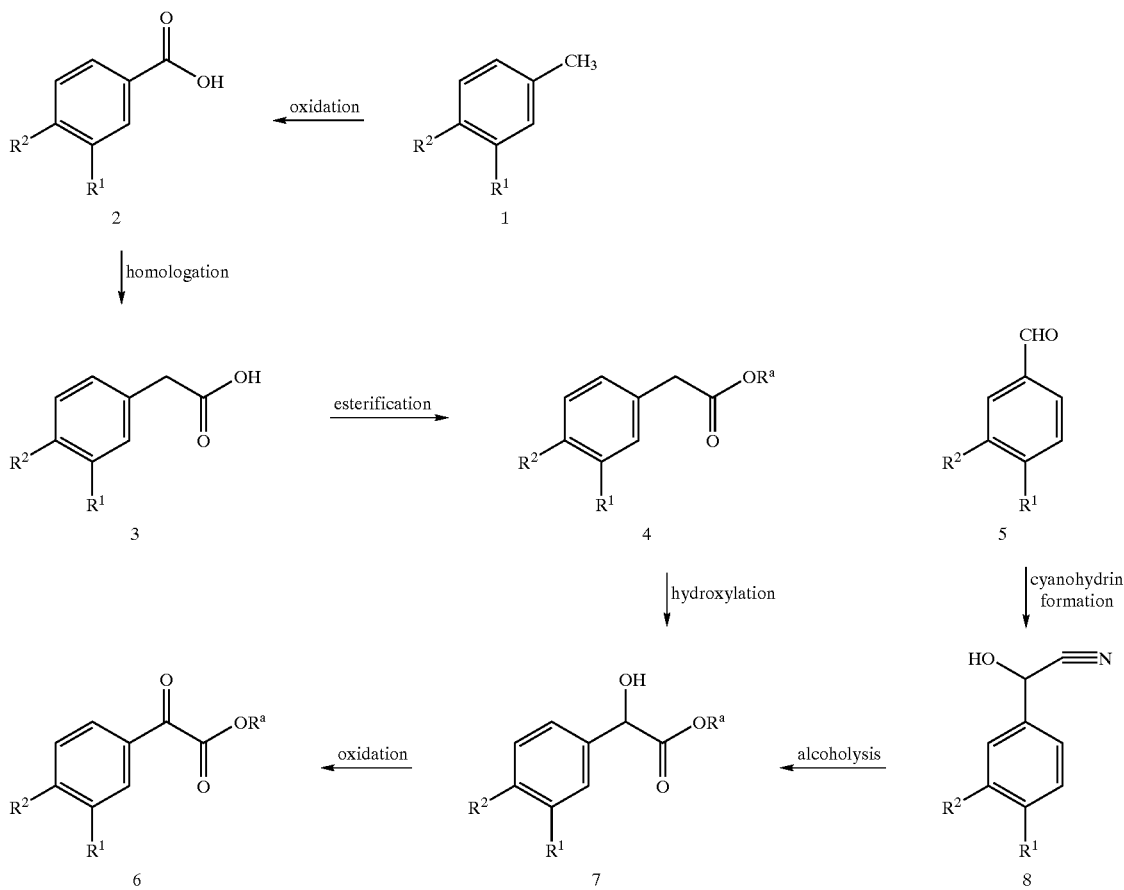

Via Friedel-Krafts Acylation

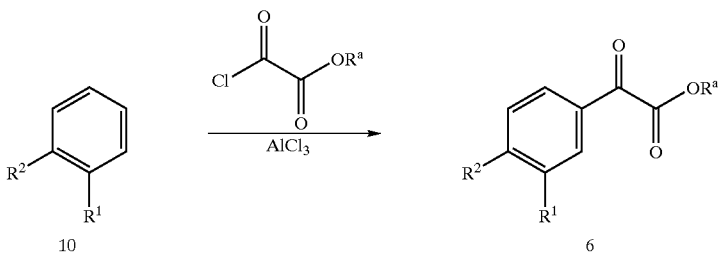

Reaction Scheme II outlines the preparation of the phenylpyruvic acid ester of formula 6, from which compounds of formula I where X=O, S, or $SO_2$ can be prepared. The compounds of formula 6 are accessible from the corresponding phenyl acetic acids of structure 3 or substituted benzenes of structure 1 as outlined in Reaction Scheme II (see for example, Anderson, J. C. and Smith, S.C. *Syn. Lett.*, 1990, 107; Davis, F. A., Haque, M. S., et al., *J. Org. Chem*, 1986, 51, 2402; Tanaka, M.; Kobayashi, T. and Sakakura, T.; *Angew. Chem. Int. Ed. Engl*, 1984, 23, 518; Murahashi, S. and Naota, T., *Synthesis*, 1993, 433). The method to prepare the pyruvates of structure 6 via the α-hydroxy phenylacetic acids of structure 7 may be considered a general procedure regardless of the nature of the substituents $R^1$ and $R^2$, with the proviso that these substituents are protected during the process with suitable protecting groups if required. The alternative procedure, the preparation of the pyruvates of structure 6 by an electrophilic substitution reaction on the substituted benzenes of structure 10 under Friedel-Crafts, is useful for certain selected $R^1$ and $R^2$ which can be identified by the skilled chemist.

In the compounds of formula 3 wherein one of $R^1$ and $R^2$ is nitro, chloro, bromo, or iodo and the other is hydrogen, either the carboxylic acids 3 or their lower alkyl esters 4 ($R^a$=lower alkyl) are commercially available. In those cases where the available starting acids of formula 3 or the commercially available potential progenitors 1,3, or 5 do not carry the desired substituents, that is, $R^1$ and $R^2$ do not fall within the scope of the all definitions listed herein for $R^1$ and $R^2$, the substituents of the available starting materials can be manipulated by any of the commonly known methods to interconvert aromatic substituents to ultimately lead to the desired substitution pattern in the phenylpyruvates of structure 6 i.e., for all definitions of $R^1$ and $R^2$. In cases where only the carboxylic acids of structure 3 are available, they can be converted to the corresponding esters 4 of lower alkyl alcohols using any conventional esterification methods. All the substituent interconversion reactions discussed heretoforward are carried out on lower alkyl esters of the compounds of formula 4.

The amino substituted compounds of formula 4 which in turn can be obtained from the corresponding $NO_2$ compound which can be diazotized to yield the corresponding diazonium compound, which in situ can be reacted with the desired lower alkyl thiol, perfluoro-lower alkyl thiol (see for example, Baleja, J. D. *Synth. Comm.* 1984, 14, 215; Giam, C. S.; Kikukawa, K., *J. Chem. Soc, Chem. Comm.* 1980, 756; Kau, D.; Krushniski, J. H.; Robertson, D. W, *J. Labelled Compd Rad.* 1985, 22, 1045; Oade, S.; Shinhama, K.; Kim, Y. H., *Bull Chem Soc. Jpn.* 1980, 53, 2023; Baker, B. R.; et al, *J. Org. Chem.* 1952, 17, 164), or alkaline earth metal cyanide, to yield corresponding compounds of formula 4, where one of the substituents is lower alkyl thio, perfluoro-lower alkyl thio, or cyano, and the other is hydrogen. If desired, the lower alkyl thio or perfluoro-lower alkyl thio compounds can then be converted to the corresponding lower alkyl sulfonyl or perfluoro-lower alkyl sulfonyl substituted compounds of formula 4. Any conventional method of oxidizing alkyl thio substituents to sulfones can be utilized to effect this conversion.

In the compounds of formula 3 wherein both of $R^1$ and $R^2$ are chloro or fluoro, the carboxylic acids 4 or the corresponding lower alkyl esters of structure 4 are commercially available. In cases where only the carboxylic acids are available, they can be converted to the corresponding esters of lower alkyl alcohols using any conventional esterification method. As shown in Reaction Scheme II, to produce the compound of formula 3 where both $R^1$ and $R^2$ are nitro, 3,4-dinitrotoluene ($R^1$=$R^2$=$NO_2$) can be used as starting material. This can be converted to the corresponding 3,4-dinitrobenzoic acid 2. Any conventional method of converting an aryl methyl group to the corresponding benzoic acid can be utilized to effect this conversion (see for example, Clark, R. D.; Muchowski, J. M.; Fisher, L. E.; Flippin, L. A.; Repke, D. B.; Souchet, M, *Synthesis*, 1991, 871). The benzoic acids of structure 2 can be homologated to the corresponding phenyl acetic acids of structure 3 by the well-known Arndt Eistert method.

The compounds of formula 4b where both $R^1$ and $R^2$ substituents are amino can be obtained from the corresponding di-nitro compound of formula 4a, described above. Any conventional method of reducing a nitro group to an amine can be utilized to effect this conversion. The compound of formula 4b where both $R^1$ and $R^2$ are amine groups can be used to prepare the corresponding compound of formula 4d where both $R^1$ and $R^2$ are iodo, bromo, chloro, or fluoro via the diazotization reaction intermediate 4c described before. Any conventional method of converting amino group to an iodo or bromo group (see for example, Lucas, H. J.; Kennedy, E. R. *Org. Synth. Coll. Vol, II* 1943, 351) can be utilized to effect this conversion.

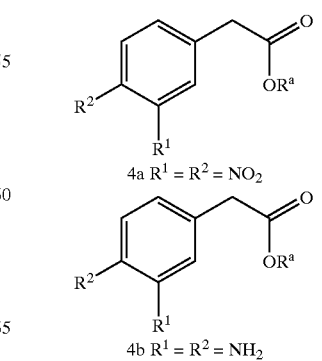

4a $R^1 = R^2 = NO_2$

4b $R^1 = R^2 = NH_2$

-continued

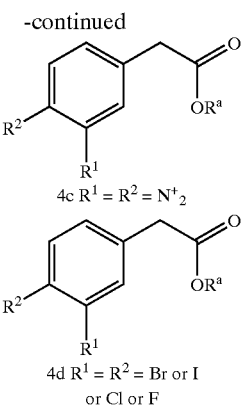

4c R¹ = R² = N⁺₂

4d R¹ = R² = Br or I or Cl or F

If it is desired to produce compounds of formula 4e,f, where both R¹ and R² are lower alkyl thio or perfluoro-lower alkyl thio groups, the compound of formula 4b where R¹ and R² are amino can be used as starting material. Any conventional method of converting an aryl amino group to aryl thioalkyl group can be utilized to effect this conversion. If it is desired to produce compounds of formula 4g,h where R¹ and R² are lower alkyl sulfonyl or perfluoro-lower alkyl sulfonyl, the corresponding compounds of formula 4e,f where R¹ and R² are lower alkyl thio or perfluoro-lower alkyl thio can be used as starting material. Any conventional method of oxidizing alkyl thio substituents to sulfones can be utilized to effect this conversion.

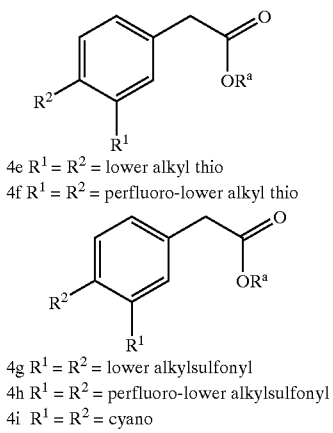

4e R¹ = R² = lower alkyl thio
4f R¹ = R² = perfluoro-lower alkyl thio

4g R¹ = R² = lower alkylsulfonyl
4h R¹ = R² = perfluoro-lower alkylsulfonyl
4i R¹ = R² = cyano If it is desired to produce compounds of formula 4i, where both R¹ and R² are cyano groups, the compound of formula 4b can be used as starting material. Any conventional method used to convert an amino group to cyano group can be utilized to effect this conversion.

The carboxylic acids of formula 3 where one of R¹ and R² is nitro and the other is halo (for example chloro) are known from the literature (see for 4-chloro-3-nitrophenyl acetic acid, Tadayuki, S.; Hiroki, M.; Shinji, U.; Mitsuhiro, S. Japanese patent, JP 71-99504, *Chemical Abstracts* 80:59716; see for 4-nitro-3-chlorophenyl acetic acid, Zhu, J.; Beugelmans, R.; Bourdet, S.; Chastanet, J.; Roussi, G. *J. Org. Chem.* 1995, 60, 6389; Beugelmans, R.; Bourdet, S.; Zhu, J. *Tetrahedron Lett.* 1995, 36, 1279). These carboxylic acids can be converted to the corresponding lower alkyl esters 4m,n using any conventional esterification methods. Thus, if it is desired to produce the compound of formula 4 where one of R¹ and R² is nitro and the other is lower alkyl thio (4o,p) or perfluoro-lower alkyl thio (4q,r), the corresponding compound where one of R¹ and R² is nitro and the other is chloro can be used as starting material. In this reaction, any conventional method of nucleophilic displacement of aromatic chlorine group with a lower alkyl thiol can be used (see for example, Singh, P.; Batra, M. S.; Singh, H, *J. Chem. Res.* —S 1985 (6), S204; Ono, M.; Nakamura, Y.; Sata, S.; Itoh, I, *Chem. Lett,* 1988, 1393; Wohrle, D.; Eskes, M.; Shigehara, K.; Yamada, A, *Synthesis,* 1993, 194; Sutter, M.; Kunz, W, US patent, U.S. Pat. No. 5,169,951). Once the compounds of formula 4 where one of R¹ and R² is nitro and the other is lower alkyl thio or perfluoro-lower alkyl thio are available, they can be converted to the corresponding compounds of formula 4 wherein one of R¹ and R² is nitro and the other is lower alkyl sulfonyl (4s,t) or perfluoro-lower alkyl sulfonyl (4u,v) using conventional oxidation procedures.

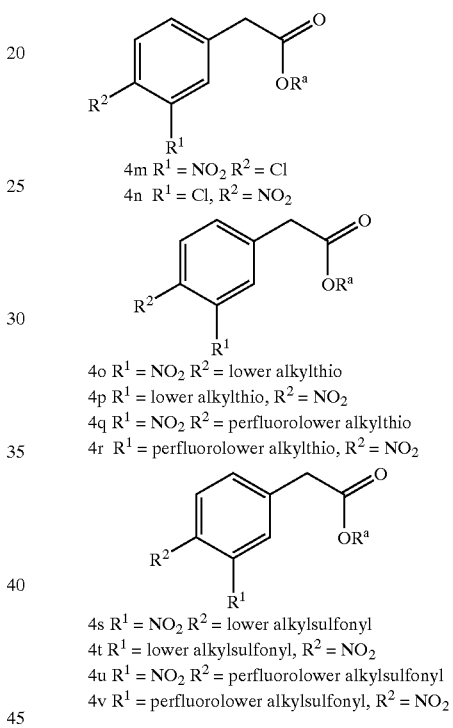

4m R¹ = NO₂ R² = Cl
4n R¹ = Cl, R² = NO₂

4o R¹ = NO₂ R² = lower alkylthio
4p R¹ = lower alkylthio, R² = NO₂
4q R¹ = NO₂ R² = perfluorolower alkylthio
4r R¹ = perfluorolower alkylthio, R² = NO₂

4s R¹ = NO₂ R² = lower alkylsulfonyl
4t R¹ = lower alkylsulfonyl, R² = NO₂
4u R¹ = NO₂ R² = perfluorolower alkylsulfonyl
4v R¹ = perfluorolower alkylsulfonyl, R² = NO₂

If it is desired to produce compounds of formula 4aa–ad where one of R¹ and R² is lower alkyl thio and the other is perfluoro-lower alkyl thio, the corresponding compound where one of R¹ and R² is amino and the other is lower alkylthio (4w,x) or perfluoro-lower alkylthio (4y,z) can be used as starting materials. Any conventional method of diazotizing an aromatic amino group and reacting it in situ with the desired lower alkyl thiol or perfluoroalkyl thiol can be utilized to effect this conversion.

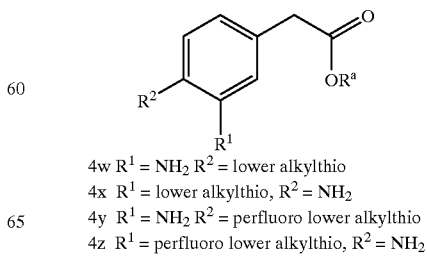

4w R¹ = NH₂ R² = lower alkylthio
4x R¹ = lower alkylthio, R² = NH₂
4y R¹ = NH₂ R² = perfluoro lower alkylthio
4z R¹ = perfluoro lower alkylthio, R² = NH₂

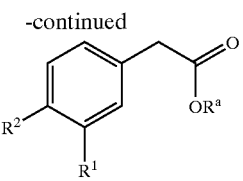

4aa $R^1$ = perfluoro lower alkylthio $R^2$ = lower alkylthio
4ab $R^1$ = lower alkylthio, $R^2$ = perfluoro lower alkylthio
4ac $R^1$ = lower alkylthio $R^2$ = perfluoro lower alkylthio
4ad $R^1$ = perfluoro lower alkylthio, $R^2$ = lower alkylthio If it is desired to produce compounds of formula 4 where one of $R^1$ and $R^2$ is lower alkyl sulfonyl and the other is perfluoro-lower alkyl sulfonyl, (4ae–4ah) the corresponding compounds (4aa–ad) where one of $R^1$ and $R^2$ is lower alkyl thio and the other is perfluoro-lower alkyl thio, can be used as starting materials. Any conventional method of oxidizing an aromatic thio ether group to the corresponding sulfone group can be utilized to effect this conversion.

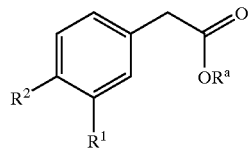

4ae $R^1$ = perfluoro lower alkylsulfonyl $R^2$ = lower alkylsulfonyl
4af $R^1$ = lower alkylsulfonyl, $R^2$ = perfluoro lower alkylsulfonyl
4ag $R^1$ = lower alkylsulfonyl $R^2$ = perfluoro lower alkylsulfonyl
4ah $R^1$ = perfluoro lower alkylsulfonyl, $R^2$ = lower alkylsulfonyl If it is desired to produce compounds of formula 4 where one of $R^1$ and $R^2$ is halo and the other is lower alkyl thio 4ai,aj) or perfluoro-lower alkyl thio (4ak,al), the corresponding compounds where one of $R^1$ and $R^2$ is amino and the other is lower alkyl thio (4w,x) or perfluoro-lower alkyl thio (4y,z) can be used as starting materials. Any conventional method of diazotizing an aromatic amino group and conversion of it in situ to an aromatic halide can be utilized to effect this conversion.

If it is desired to produce compounds of formula 4 where one of $R^1$ and $R^2$ is cyano, and the other is halo, (4aq, 4ar), the corresponding compounds of formula (4as, 4at) where one of $R^1$ and $R^2$ is nitro, and the other is amino can be used as starting materials. This transformation can be achieved via conversion of amino group of compounds of formula (4as, 4at) to corresponding halo compounds (4au, 4av), which in turn further can be transformed to the compounds of formula (4aq, 4ar).

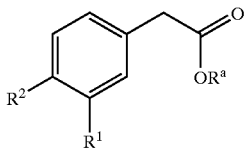

4ai $R^1$ = Halogen $R^2$ = lower alkylthio
4aj $R^1$ = lower alkylthio, $R^2$ = Halogen
4ak $R^1$ = Halogen $R^2$ = perfluoro lower alkylthio
4al $R^1$ = perfluoro lower alkylthio, $R^2$ = Halogen If it is desired to produce compounds of formula 4 where one of $R^1$ and $R^2$ is cyano, and the other is lower alkylthio or lower perfluoro lower alkylthio (4ba–4be), the corresponding compounds of formula 4as, 4at can be used as starting material. Any conventional means of converting an amino group to a thioalkyl group can be used to affect this conversion.

If it is desired to produce compounds of formula 4 where one of $R^1$ and $R^2$ is cyano and the other is lower alkylsulfonyl or perfluoro-loweralkylsulfonyl (4bf–4bi), the corresponding compounds of formula (4ba–4be) can be used as starting material. Any conventional means of converting a thio ether to the corresponding sulfone can be used to affect this conversion.

If it is desired to produce compounds of formula 4 where one of $R^1$ and $R^2$ is halo and the other is lower alkyl sulfonyl or perfluoro-lower alkyl sulfonyl, (4am–4ap) the corresponding compounds where one of $R^1$ and $R^2$ is halo and the other is lower alkyl thio (4ai,aj) or perfluoro-lower alkyl thio (4ak,al) can be used as starting materials. Any conventional method of oxidizing an aromatic thio ether to the corresponding sulfone can be utilized to effect this conversion.

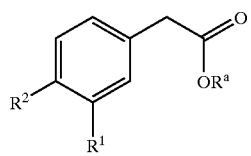

4am $R^1$ = Halogen $R^2$ = lower alkylsulfonyl
4an $R^1$ = lower alkylsulfonyl, $R^2$ = Halogen
4ao $R^1$ = Halogen $R^2$ = perfluoro lower alkylsulfonyl
4ap $R^1$ = perfluoro lower alkylsulfonyl, $R^2$ = Halogen
4aq $R^1$ = cyano, $R^2$ = halo
4ar $R^1$ = halo, $R^2$ = cyano
4as $R^1$ = nitro; $R^2$ = amino
4at $R^1$ = amino, $R^2$ = nitro
4au $R^1$ = nitro; $R^2$ = halo
4av $R^1$ = halo; $R^2$ = nitro

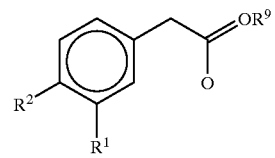

4ba $R^1$ = CN; $R^2$ = lower alkylthio
4bc $R^1$ = lower alkylthio, $R^2$ = CN
4bd $R^1$ = CN; $R^2$ = perfluoro lower alkylthio
4be $R^1$ = perfluoro lower alkylthio, $R^2$ = CN
4bf $R^1$ = CN, $R^2$ = lower alkylsulfone
4bg $R^1$ = lower alkyl sulfone, $R^2$ = CN
4bh $R^1$ = CN; $R^2$ = perfluoro lower alkyl sulfone
4bi $R^1$ = perfluoro lower alkylsulfone; $R^2$ = CN In cases where one or both of $R^1$ or $R^2$ is an amino group in compounds of structure 6, the amino groups are protected with a conventional amino protecting group, before further transformations are carried out.

Preparation of compounds of formula I where X is O or S is outlined in Reaction Scheme I. The pyruvate esters of formula 6 are transformed to the corresponding aryl sulfonyl hydrazones of formula 9 by reacting the pyruvate esters with the appropriate sulfonylhydrazide derivative. This reaction is conveniently carried out by conventional aryl sulfonyl hydrazide condensation reaction conditions, for example by refluxing a solution of the pyruvate ester 6 and p-toluenesulfonyl hydrazide in an inert solvent, preferably an aromatic hydrocarbon, for example benzene or toluene, preferably toluene. The reaction may be performed in an apparatus designed such that the refluxing solvent, which contains the azeotroped reaction byproduct, water, to pass though a water removing agent, such as molecular sieves, before returning to the reaction flask. In this manner, the hydrazone forming reaction may be accelerated and driven to completion. The p-toluenesulfonylhydrazones of formula 9, can then be treated with an tertiary amine base in a polyhalogenated organic solvent, for example triethylamine or diisopropylethylamine, preferably triethylamine in a chlorinated hydrocarbon solvent, for example dichloromethane, to give the corresponding diazo esters of formula II. This conversion is normally carried out at a temperature of between zero degrees and 40° C., preferably at the ambient temperature.

Compounds of structure 12 where X is O may be prepared by reacting the diazo ester of formula II with the appropriate cycloalkyl, cycloalkenyl or non-aromatic heterocyclic alcohol in the presence of catalytic amount of rhodium (II) acetate. The reaction is conveniently carried in an inert solvent, preferably dichloromethane at a temperature of between zero degrees and 40° C., preferably at room temperature.

In a like manner, compounds of structure 12, where X is S, may be prepared by reacting the diazo ester of formula II with the appropriate cycloalkyl, cycloalkenyl or non-aromatic heterocyclic mercaptan in the presence of catalytic amount of rhodium (II) acetate. The reaction is conveniently carried in an inert solvent, preferably dichloromethane at a temperature of between zero degrees and the reflux temperature of the mixture, preferably at the reflux temperature.

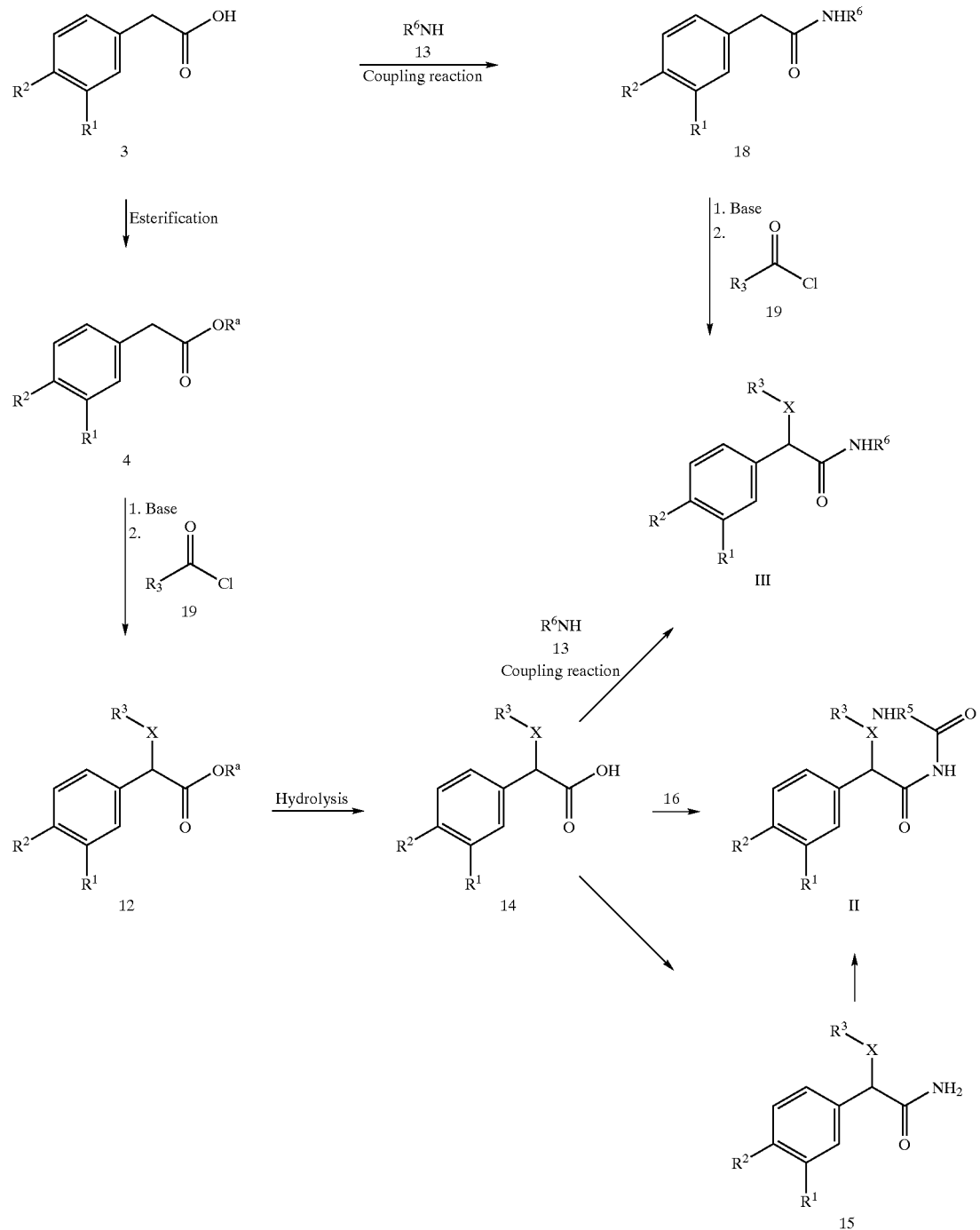

Reaction Scheme III

Preparation of compounds of formula I where X is C(O) is outlined in Reaction Scheme I. More specifically, two related methods are utilized to prepare compounds of structure III, as shown in Reaction Scheme III, where X is C(O). In the first method, the phenylacetic acids of structure 3 are first converted to the corresponding ester 4 by any of the methods well known to those of normal competence in the field of organic chemistry. As an example, an acid of structure 3 in an inert solvent, for example methanol or diethyl ether or tetrahydrofuran or a mixture thereof, may be treated with an excess of an ethereal solution of diazomethane, or treatment of acid 3 with methanol in the presence of a catalytic amount of sulfuric acid.

The thus formed ester of structure 4 may be deprotonated by with a non-nucleophilic strong base, for example lithium diisopropylamide or lithium bis(trimethylsilyl)amide, in an inert solvent, for example diethyl ether or tetrahydrofuran, preferably tetrahydrofuran. The deprotonation reaction may be conveniently carried out in an inert atmosphere under ardhydrous conditions at a temperature of from −50° C. to −100° C., preferably at −78° C. The lithiated species formed in this manner, may be reacted in situ with a cycloalkyl or cycloalkenyl acid chloride of structure 19 while the reaction temperature may be maintained at a temperature of from −50° C. to −100° C., preferably at −78° C. to give the compound of structure 12, where X=C(O).

Cleavage of the alkali-labile ester moiety in compounds of structure 12 ($R^a$=unbranched lower alkyl) may be carried out in accordance with known procedures. For example, the esters of structure 12, are treated with an alkali metal hydroxide, for example potassium hydroxide, sodium hydroxide or lithium hydroxide, preferably potassium hydroxide in an inert solvent system, for example a mixture of ethanol and water. The saponification reaction may be generally performed at a temperature of from zero degrees to the reflux temperature of the mixture, preferably at room temperature, to furnish the acids of structure 14.

The coupling of carboxylic acids of structure 14 with the amines $R^6$—$NH_2$ (13) to give the amides of structure III can be performed by using methods well known to one of ordinary skill in the art. For example, the reaction may be conveniently carried out by treating the carboxylic acid of structure 14 with the amine 13 in the presence of a tertiary amine base, for example triethylamine or diethylisopropylamine and a coupling agent such as O—(1H-benzotriazo-1-yl)-1,1,3,3,-tetramethyluronium hexafluorophosphate (HBTU) or benzotriazol-1-yloxy(dimethylamino) phosphonium hexafluorophosphate (BOP). The reaction may be carried out in an inert solvent, such as a chlorinated hydrocarbon (e.g., dichloromethane) or N,N-dimethylformamide at a temperature between zero degrees and about room temperature, preferably at about room temperature, optionally in the presence of a substance that accelerates the rate of reaction, for example 1-hydroxybenzotriazole.

Alternatively, to prepare the amides of structure III, as shown in scheme III, the carboxylic acids of structure 3 can be activated through conversion to a mixed anhydride, which may be in turn reacted with the amine 13 in the presence of a catalyst to afford the amides of structure 18, or by using standard peptide coupling reagents such as HBTU. Subsequently the amide of structure 18 may be deprotonated by with a non-nucleophilic strong base, for example lithium diisopropylamide or lithium bis(trimethylsilyl)amide, in an inert solvent, for example diethyl ether or tetrahydrofuran, preferably tetrahydrofuran. The deprotonation reaction may be conveniently carried out in an inert atmosphere under anhydrous conditions at a temperature of from −50° C. to −100° C., preferably at −78° C. The thus formed lithiated intermediate, may be reacted in situ with a cycloalkyl or cycloalkenyl acid chloride of structure 19 while the reaction temperature may be maintained at a temperature of from −50° C. to −100° C., preferably at −78° C. to give the compound of structure III, where X=C(O).

To produce the primary amides of structure 15, the carboxylic acids of structure 14 are converted to an activated species, preferably an acid chloride which in turn may be reacted with a protected form of ammonia, hexamethyldisilazane, to give after hydrolytic removal if the trimethylsilyl groups in situ, the primary amides. The carboxylic acids of structure 14 are transformed into the corresponding acid chlorides on treatment with oxalyl chloride in an inert solvent, such as a chlorinated hydrocarbon (e.g., dichloromethane) or an aromatic hydrocarbon such as benzene. The reaction may be carried out in the presence of a catalytic amount of N,N-dimethylformamide at a temperature of between zero degrees and about room temperature, preferably at about zero degrees. The subsequent reaction of the intermediate acid chloride with an excess of 1,1,1,3,3,3-hexamethyldisilazane may be carried out in situ at a temperature between zero degrees and about room temperature, preferably at about room temperature. Treatment of the formed bis(trimethylsilyl)amide with a large excess of methanol containing 5% sulfuric acid at room temperature provides the desilylated primary amide of structure 15.

The ureas of structure II are produced by three methods:
(a) reaction of the acid chlorides derived as described above from the carboxylic acids of structure 14 with a monosubstituted urea 16
(b) by reaction of the primary amide of structure 15 with and isocyanate of structure 17
(c) by reaction of esters of formula 12 ($R^a$+lower alkyl) with a monosubstituted urea (16) in the presence of an alkali metal alkoxide.

In the first mentioned procedure, the acid chloride, derived from the carboxylic acid of structure 14 on treatment with oxalyl chloride is as described above except the reaction may be run in fluorobenzene, may be reacted in situ with urea or a monosubstituted urea (16). The reaction may be carried out at a temperature between 50° C. and about the reflux temperature of the mixture, preferably at about 70° C. to yield the ureas of structure II. In the alternative scheme, the primary amide of structure 15 may be reacted with an isocyanate of structure 17, in an inert solvent such as an aromatic hydrocarbon, preferably toluene. The reaction may be normally carried out at a temperature between 50° C. and about the reflux temperature of the mixture, preferably at the reflux temperature to yield the ureas of structure II.

For compounds of formula I where X is S, the thioethers of structure II and III (X=S) may be converted to the sulfones of structure I (X=$SO_2$) by using methods well known to one of ordinary skill in the field of organic chemistry. For example, the transformation may be achieved by using a two-step procedure. In the first step, treatment of the thio ethers of structures II and III (X=S) with an oxidizing agent, preferably sodium periodate in aqueous methanol furnished the intermediate sulfoxides of structure II and III (X=SO). The reaction may be conveniently carried out at a temperature of between zero degrees and about room temperature, preferably at about room temperature. In the second step, treatment of the intermediate sulfoxides II and III (X=SO) with an oxidizing agent, preferably potassium permanganate in aqueous methanol furnished the sulfones of structure I (X=SO$_2$). The reaction may be conveniently carried out at a temperature of between zero degrees and about room temperature, preferably at about room temperature.

The compound of formula I has an asymmetric carbon atom through which the group XR$^3$ and the acid amide substituents are connected. In accordance with this invention, the preferred stereoconfiguration of this group is R, except in cases where X is carbonyl, where the preferred enantiomer is "S". In cases wherein R$^3$ is asymmetric (e.g. cycloalkene), an additional chiral center at the ring carbon connecting with atom 'X' is generated. At this center, racemic compounds and compounds corresponding to both R and S configuration are part of this invention.

If it is desired to produce the R or the S isomer of the compound of formula I, this compound can be separated into these isomers by any conventional chemical means. Among the preferred chemical means is to react the compound of formula 14 (same as 14 above) with an optically active base. Any conventional optically active base can be utilized to carry out this resolution. Among the preferred optically active bases are the optically active amine bases such as alpha-methylbenzylamine, quinine, dehydroabietylamine and alpha-methylnaphthylamine. Any of the conventional techniques utilized in resolving organic acids with optically active organic amine bases can be utilized in carrying out this reaction.

In the resolution step, the compound of formula 14 is reacted with the optically active base in an inert organic solvent medium to produce salts of the optically active amine with both the R and S isomers of the compound of formula 14. In the formation of these salts, temperatures and pressure are not critical and the salt formation can take place at room temperature and atmospheric pressure. The R and S salts can be separated by any conventional method such as fractional crystallization. After crystallization, each of the salts can be converted to the respective compounds of formula 14 in the R and S configuration by hydrolysis with an acid. Among the preferred acids are dilute aqueous acids, i.e., from about 0.001N to 2N aqueous acids, such as aqueous sulfuric or aqueous hydrochloric acid. The configuration of formula 14 which is produced by this method of resolution is carried out throughout the entire reaction scheme to produce the desired R or S isomer of formula I.

The separation of R and S isomers can also be achieved using an enzymatic ester hydrolysis of any lower alkyl esters corresponding to the compound of the formula 14 (see for example, Ahmar, M.; Girard, C.; Bloch, R, *Tetrahedron Lett*, 1989, 7053), which results in the formation of corresponding chiral acid and chiral ester. The ester and the acid can be separated by any conventional method of separating an acid from an ester. The preferred method of resolution of racemates of the compounds of the formula 14 is via the formation of corresponding diastereomeric esters or amides. These diastereomeric esters or amides can be prepared by coupling the carboxylic acids of the formula 14 with a chiral alcohol, or a chiral amine. This reaction can be carried out using any conventional method of coupling a carboxylic acid with an alcohol or an amine. The corresponding diastereomers of compounds of the formula 14 can then be separated using any conventional separation methods. The resulting pure diastereomeric esters or amides can then be hydrolyzed to yield the corresponding pure R or S isomers. The hydrolysis reaction can be carried out using any conventional method to hydrolyze an ester or an amide without racemization.

On the basis of their capability of activating glucokinase, the compounds of above formula I can be used as medicaments for the treatment of type II diabetes. Therefore, as mentioned earlier, medicaments containing a compound of formula I are also an object of the present invention, as is a process for the manufacture of such medicaments, which process comprises bringing one or more compounds of formula I and, if desired, one or more other therapeutically valuable substances into a galenical administration form, e.g. by combining a compound of formula I with a pharmaceutically acceptable carrier and/or adjuvant.

The pharmaceutical compositions may be administered orally, for example in the form of tablets, coated tablets, dragees, hard or soft gelatine capsules, solutions, emulsions or suspensions. Administration can also be carried out rectally, for example using suppositories; locally or percutaneously, for example using ointments, creams, gels or solutions; or parenterally, e.g. intravenously, intramuscularly, subcutaneously, intrathecally or transdermally, using for example injectable solutions. Furthermore, administration can be carried out sublingually or as an aerosol, for example in the form of a spray. For the preparation of tablets, coated tablets, dragees or hard gelatine capsules the compounds of the present invention may be admixed with pharmaceutically inert, inorganic or organic excipients. Examples of suitable excipients for tablets, dragees or hard gelatine capsules include lactose, maize starch or derivatives thereof, talc or stearic acid or salts thereof. Suitable excipients for use with soft gelatine capsules include for example vegetable oils, waxes, fats, semi-solid or liquid polyols etc.; according to the nature of the active ingredients it may however be the case that no excipient is needed at all for soft gelatine capsules. For the preparation of solutions and syrups, excipients that may be used include for example water, polyols, saccharose, invert sugar and glucose. For injectable solutions, excipients that may be used include for example water, alcohols, polyols, glycerine, and vegetable oils. For suppositories, and local or percutaneous application, excipients that may be used include for example natural or hardened oils, waxes, fats and semi-solid or liquid polyols. The pharmaceutical compositions may also contain preserving agents, solubilising agents, stabilising agents, wetting agents, emulsifiers, sweeteners, colorants, odorants, salts for the variation of osmotic pressure, buffers, coating agents or antioxidants. As mentioned earlier, they may also contain other therapeutically valuable agents. It is a prerequisite that all adjuvants used in the manufacture of the preparations are non-toxic.

Preferred forms of use are intravenous, intramuscular or oral administration, most preferred is oral administration. The dosages in which the compounds of formula (a) are administered in effective amounts depend on the nature of the specific active ingredient, the age and the requirements of the patient and the mode of application. In general, dosages of about 1–100 mg/kg body weight per day come into consideration.

All of the compounds described in the following syntheses activated glucokinase in vitro in accordance with the assay described in the Biological Activity Example.

This invention will be better understood from the following examples, which are for purposes of illustration and are not intended to limit the invention defined in the claims that follow thereafter.

EXAMPLES

Example 1

Preparation of rac-2-cyclopentyloxy-2-(3,4-dichloro-phenyl)-N-thiazol-2-yl-acetamide

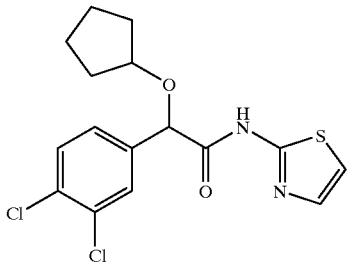

A solution of aluminum chloride (19.96 g 149.6 mmol) in dichloromethane (85 mL) was cooled to 0° C. and then methyl oxalyl chloride (6.6 mL 71.43 mmol) was slowly added and the mixture was stirred at 0–5° C. for 1 h. 1,2-dichlorobenzene (7.7 mL, 68.03 mmol) was added, while the reaction temperature was maintained below 5° C. throughout the addition. After the mixture was stirred at 0–5° C. for an additional 1 h, it was allowed to warm to 25° C. and stirred at that temperature for 16 h. The reaction was then poured slowly into an ice/water slurry and extracted with dichloromethane (3×50 mL). The combined organic layers were dried over sodium sulfate and evaporated under reduced pressure to give a yellow solid. The product was purified by flash chromatography (Merck Silica gel 60, 230–400 mesh, 90/10 hexanes/ethyl acetate) to provide (3,4-dichloro-phenyl)-oxo-acetic acid methyl ester (1.59 g, 10% yield) as a yellow solid: EI-HRMS m/e calcd for $C_9H_6O_3Cl_2$ (M$^+$) 231.9694, found 231.9698.

To a dry round bottom flask, fitted with a Dean Stark: trap filled with 3 Å molecular sieves and a reflux condenser, under argon was placed (3,4-dichloro-phenyl)-oxo-acetic acid methyl ester (1.00 g, 4.29 mmol)) and p-toluenesulfonylhydrazide (1.03 g, 4.29 mmol) in toluene (20 mL). The reaction was heated at 110° C. for 16 h, then was cooled to 25° C. and the solvent removed in vacuo to yield a light yellow solid. The product was crystallized from hot methanol to afford (3,4-dichloro-phenyl)-(4-toluenesulfonylhydrazono)-acetic acid methyl ester (1.45 g, 84% yield) as an off white solid: EI-HRMS m/e calcd $C_{16}H_{14}Cl_2N_2O_4S$ (M$^+$) 400.0051, found 400.0057.

In a dry flask under argon was placed a solution of (3,4-dichloro-phenyl)-(4-toluenesulfonylhydrazono)-acetic acid methyl ester (1.45 g, 3.61 mmol) in dichloromethane (20 mL) containing triethylamine (0.55 mL, 3.97 mmol) at 25° C. The bright yellow solution was then stirred at 25° C. for 1 h, then the solvent was removed in vacuo to yield a bright yellow solid. The product was purified by flash chromatography (Merck Silica gel 60, 230–400 mesh, 7/1/0.5 hexanes/dichloromethane/methanol) to furnish diazo-(3,4-dichloro-phenyl)-acetic acid methyl ester (814 mg, 92% yield) as a bright yellowish orange solid: EI-HRMS m/e calcd for $C_9H_6Cl_2N_2O_2$ (M$^+$) 243.9806, found 243.9800.

In a dry flask under argon was placed diazo-(3,4-dichloro-phenyl)-acetic acid methyl ester (350 mg 1.4 mmol) to which was added dichloromethane (10 mL) and cyclopentanol (0.25 mL, 2.8 mmol). The solution was stirred at 25° C. and as rhodium (II) acetate dimer (13 mg, 0.028 mmol) was added, the immediate evolution of gas was noted and the color changed from bright yellow to an aquagreen color. After the solution was stirred at 25° C. for 1 h, it was then poured into water and the layers were separated. The aqueous layer was washed with dichloromethane (3×15 mL) and the organic layers were then combined, dried over sodium sulfate and concentrated in vacuo. The residual material was purified by flash chromatography (Merck Silica gel 60, 230–400 mesh, 95/5 hexanes/ethyl acetate) to give rac-cyclopentyloxy-(3,4-dichloro-phenyl)-acetic acid methyl ester (273 mg, 64% yield) as a clear colorless oil: EI-HRMS m/e calcd for $C_{14}H_{16}Cl_2O_3$ (M$^+$) 302.0477, found 302.0484.

A solution of rac-cyclopentyloxy-(3,4-dichloro-phenyl)-acetic acid methyl ester (266 mg, 0.877 mmol) in ethanol (10 mL) was treated with a solution of potassium hydroxide (123 mg, 2.19 mmol) in water (1 mL) and the mixture was stirred at 25° C. After 3 h, the reaction was diluted with water (5 mL) and the ethanol was removed in vacuo. The aqueous layer was then acidified to pH 2 with 1 N hydrochloric acid and extracted with dichloromethane (3×15 mL). The combined organic layers were dried over sodium sulfate, filtered and evaporated under reduced pressure. The residue was purified by flash chromatography (Merck Silica gel 60, 230–400 mesh, 95/5 chloroform/methanol plus 1% acetic acid) to afford rac-cyclopentyloxy-(3,4-dichloro-phenyl)-acetic acid (223 mg, 88% yield) as a white solid, mp 87.5–89.9 IC; EI-HRMS m/e calcd for $C_{13}H_{14}Cl_2O_3$ (M$^+$) 288.0320, found 288.0332.

A solution of rac-cyclopentyloxy-(3,4-dichloro-phenyl)-acetic acid (52 mg, 0.17 mmol) in dichloromethane (10 mL) was treated with O—(1H-benzotriazolo-1-yl)-1,1,3,3-tetramethyluronium hexafluorophosphate (HBTU) (72 mg, 0.19 mmol), diisopropyl-ethylamine (0.09 mL, 0.52 mmol) and 2-aminothiazole (26 mg, 0.25 mmol). The resulting brownish-orange solution was then stirred 16 h at 25° C. The reaction was then diluted with water (10 mL) and extracted with ethyl acetate (3×15 mL). The combined organic layers were washed with water (1×10 mL), 1N sodium hydroxide solution (1×10 mL), 1N hydrochloric acid (1×10 mL) and brine (1×10 mL), then were dried over sodium sulfate and concentrated in vacuo. The product was purified by flash chromatography (Merck Silica gel 60, 230–400 mesh, 90/10 hexanes/ethyl acetate) to furnish rac-2-cyclopentyloxy-2-(3,4-dichloro-phenyl)-N-thiazol-2-yl-acetamide (45 mg, 70% yield) as a white foam: EI-HRMS m/e calcd for $C_{16}H_{16}Cl_2O_2N_2S$ (M$^+$) 370.0309, found 370.0309.

Example 2

Preparation of rac-2-cyclohexyloxy-2-(3,4-dichloro-phenyl)-N-thiazol-2-yl-acetamide

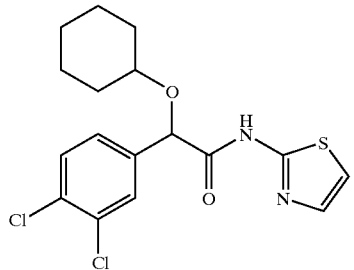

In a dry 25 mL round bottom flask under argon was placed diazo-(3,4-dichloro-phenyl)-acetic acid methyl ester (from Example 1, 550 mg 2.24 mmol) and cyclohexanol (0.47 mL, 4.49 mmol) in dichloromethane (10 mL). The solution was stirred at 25° C. and as rhodium (II) acetate dimer (20 mg, 0.045 mmol) was added, the immediate evolution of gas was observed and the color changed from bright yellow to an aquagreen color. After the solution was stirred at 25° C. for 1 h, it was poured into water and the layers were separated. The aqueous layer was washed with dichloromethane (3×15 mL) and the combined organic layers were dried over sodium sulfate and evaporated under reduced pressure. The residual oil was purified by flash chromatography (Merck Silica gel 60, 230–400 mesh, 98/2 hexanes/ethyl acetate) to furnish rac-cyclohexyloxy-(3,4-dichloro-phenyl)-acetic acid methyl ester (527 mg, 74% yield) as a clear colorless oil: EI-HRMS m/e calcd for $C_{15}H_{18}Cl_2O_3$ ($M^+$) 316.0633, found 316.0646.

A solution of rac-cyclohexyloxy-(3,4-dichloro-phenyl)-acetic acid methyl ester (527 mg, 1.66 mmol) in ethanol (15 mL) was treated with a solution of potassium hydroxide (233 mg, 4.15 mmol) in water (2 mL) and the mixture was stirred at 25° C. After 3 h, the reaction was diluted with water (5 mL), and the ethanol was removed in vacuo. The aqueous layer was then acidified to pH 2 with 1N hydrochloric acid and extracted with dichloromethane (3×15 mL). The combined organic layers were dried over sodium sulfate, filtered and concentrated in vacuo. The residual oil was purified by flash chromatography (Merck Silica gel 60, 230–400 mesh, 95/5 chloroform/methanol plus 1% acetic acid) to give rac-cyclohexyloxy-(3,4-dichloro-phenyl)-acetic acid (487 mg, 97% yield) as a colorless oil: EI-HRMS m/e calcd for $C_{14}H_{16}Cl_2O_3$ ($M^+$) 302.0477, found 302.0486.

A solution of rac-cyclohexyloxy-(3,4-dichloro-phenyl)-acetic acid (102 mg, 0.34 mmol) in dichloromethane (10 mL) was treated with benzotriazol-1-yloxy-(dimethylamino)phosphonium hexafluorophosphate (BOP) reagent (223 mg, 0.51 mmol), triethylamine (0.14 mL, 0.52 mmol), and 2-aminothiazole (51 mg, 0.51 mmol) at 25° C. After the resulting brownish-orange solution was stirred 16 h at 25° C., it was diluted with water (10 mL) and extracted with ethyl acetate (3×15 mL). The combined organic layers were washed with water (1×10 mL), 1N sodium hydroxide solution (1×10 mL), 1N hydrochloric acid (1×10 mL), and brine (1×10 mL), then were dried over sodium sulfate and evaporated in vacuo. The product was purified by flash chromatography (Merck Silica gel 60, 230–400 mesh, 90/10 hexanes/ethyl acetate) to furnish rac-2-cyclohexyloxy-2-(3,4-dichloro-phenyl)-N-thiazol-2-yl-acetamide (115 mg, 88% yield) as a white foam: EI-HRMS m/e calcd for $C_{17}H_{18}Cl_2O_2N_2S$ ($M^+$) 384.0466, found 384.0469.

Example 3

Preparation of rac-2-(cyclohex-2-enyloxy)-2-(3,4-dichloro-phenyl)-N-thiazol-2-yl-acetamide

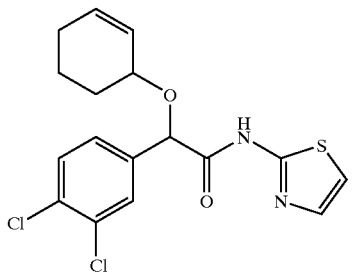

In a dry 25 mL round bottom flask under argon was placed diazo-(3,4-dichloro-phenyl)-acetic acid methyl ester (from Example 1, 552 mg, 2.25 mmol), dichloromethane (10 mL) and rac-2-cyclohexen-1-ol (0.45 mL, 4.51 mmol). The solution was stirred at 25° C. and then the rhodium (II) acetate dimer (20 mg, 0.045 mmol) was added. Gas evolution began immediately and the color changed from bright yellow to an aquagreen color. After the solution was stirred at 25° C. for a period of 1 h, it was poured into water and the layers were separated. The aqueous layer was washed with dichloromethane (3×15 mL), then the combined organic layers were dried over sodium sulfate and evaporated under reduced pressure. The residual oil was purified by flash chromatography (Merck Silica gel 60, 230–400 mesh, 98/2 hexanes/ethyl acetate to afford rac-(cyclohex-2-enyloxy)-(3,4-dichloro-phenyl)-acetic acid methyl ester (552 mg, 78% yield) as a, light yellow oil: EI-HRMS m/e calcd for $C_{15}H_{16}Cl_2O)_3$ ($M^+$) 314.0468, found 314.0476.

A solution of rac-(cyclohex-2-enyloxy)-(3,4-dichloro-phenyl)-acetic acid methyl ester (552 mg, 0.877 mmol) in ethanol (10 mL) to was treated with a solution of potassium hydroxide (246 mg, 4.37 mmol) and water (2 mL) and the mixture was stirred at 25° C. After 3 h, the reaction was diluted with water (10 mL) and the ethanol was removed in vacuo. The aqueous layer was then acidified to pH 2 with 1N hydrochloric acid and extracted with dichloromethane (3×15 mL). The combined organic layers were dried over sodium sulfate, filtered and concentrated in vacuo. The product was purified by flash chromatography (Merck Silica gel 60, 230–400 mesh, 95/5 chloroform/methanol plus 1% acetic acid) to give rac-(cyclohex-2-eyloxy)-(3,4-dichloro-phenyl)-acetic acid (520 mg, 99% yield) as a yellow oil: EI-HRMS m/e calcd for $C_{14}H_{14}Cl_2O_3$ ($M^+$) 300.0320, found 300.0324.

A solution of rac-(cyclohex-2-enyloxy)-(3,4-dichloro-phenyl)-acetic acid (89 mg, 0.28 mmol) in dichloromethane (10 mL) was treated with BOP reagent (187 mg, 0.42 mmol), triethylamine (0.12 mL, 0.85 mmol), and 2-aminothiazole (42 mg, 0.42 mmol) at 25° C. The resulting brownish-orange solution was then stirred 16 h at 25° C., then was diluted with water (10 mL) and extracted with ethyl acetate (3×15 mL). The combined organic layers were washed with water (1×10 mL), 1N sodium hydroxide solution (1×10 mL), 1N hydrochloric acid (1×10 mL), and brine (1×10 mL), then were dried over sodium sulfate and evaporated in vacuo. The residue was purified by flash chromatography (Merck Silica gel 60, 230–400 mesh, 95/5 hexanes/ethyl acetate) to provide rac-(cyclohex-2-enyloxy)-2-(3,4-dichloro-phenyl)-N-thiazol-2-yl-acetamide (99 mg, 92% yield) as a white foam: EI-HRMS m/e calcd for $C_{17}H_{16}Cl_2O_2N_2S$ ($M^+$) 382.0309, found 382.0308.

Example 4

Preparation of rac-2-(3,4-dichloro-phenyl)-2-[(tetrahydro-pyran-4-yl)oxy]-N-thiazol-2-yl-acetamide

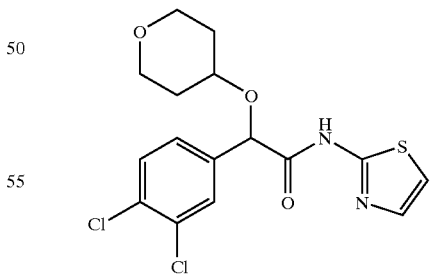

In a dry 25 mL round bottom flask under argon was placed diazo-(3,4-dichloro-phenyl)-acetic acid methyl ester (from Example 1, 614 mg, 2.51 mmol), dichloromethane (10 mL) and tetrahydro-4H-pyran-4-ol (0.50 mL, 5.01 mmol). The solution was stirred at 25° C. and then rhodium (II) acetate dimer (22 mg, 0.05 mmol) was added. Gas evolution began immediately and the color changed from bright yellow to an aquagreen color. After the solution was stirred at 25° C. for 1 h, it was poured into water (10 mL) and the layers were separated. The aqueous layer was washed with dichloromethane (3×15 mL) and the combined organic layers were dried over sodium sulfate and in vacuo. The residual material was purified by flash chromatography (Merck Silica gel 60, 230–400 mesh, 98/2 hexanes/ethyl acetate) to furnish rac-(3,4-dichloro-phenyl)-[(tetrahydro-pyran-4-yl)oxy]-acetic acid methyl ester (598 mg, 75% yield) as a clear colorless oil: EI-HRMS m/e calcd for $C_{14}H_{16}Cl_2O_4$ (M$^+$) 318.0426, found 318.0412.

A solution of rac-(3,4-dichloro-phenyl)-[(tetrahydro-pyran-4-yl)oxy]-acetic acid methyl ester (598 mg, 1.87 mmol) in ethanol (15 mL) was treated with a solution of potassium hydroxide (262 mg, 4.68 mmol) and water (2 mL) and the mixture was allowed to stir at 25° C. After 3 h, the reaction was diluted with water (10 mL) and the ethanol was removed in vacuo. The aqueous layer was then acidified to pH 2 with 1N hydrochloric acid and extracted with dichloromethane (3×15 mL). The combined organic layers were dried over sodium sulfate, filtered and evaporated under reduced pressure. The reaction product was purified by flash chromatography (Merck Silica gel 60, 230–400 mesh, 95/5 chloroform/methanol plus 1% acetic acid) to afford rac-(3, 4-dichloro-phenyl)-[(tetrahydro-pyran-4-yl)oxy]-acetic acid (544 mg, 95% yield) as a clear colorless oil: EI-HRMS m/e calcd for $C_{13}H_{14}Cl_2O_4$ (M$^+$) 304.0269, found 304.0259.

A solution of rac-(3,4-dichloro-phenyl)-[(tetrahydro-pyran-4-yl)oxy]-acetic acid (90 mg, 0.30 mmol) in dichloromethane (10 mL) was treated with BOP reagent (195 mg, 0.44 mmol), triethylamine (0.12 mL, 0.88 mmol), and 2-aminothiazole (44 mg, 0.44 mmol) at 25° C. After the resulting brownish-orange solution was stirred 16 h at 25° C., it was diluted with water (10 ml) and extracted with ethyl acetate (3×15 mL). The combined organic layers were washed with water (1×10 mL), 1N sodium hydroxide solution (1×10 mL), 1N hydrochloric acid (1×10 mL) and brine (1×10 mL), then were dried over sodium sulfate and evaporated in vacuo. The residual material was purified by flash chromatography (Merck Silica gel 60, 230–400 mesh, 90/10 hexanes/ethyl acetate) to give rac-2-(3,4-dichloro-phenyl)-2-[(tetrahydro-pyran-4-yl)oxy]-N-thiazol-2-yl-acetamide (98 mg, 86% yield) as a white foam: EI-HRMS m/e calcd for $C_{16}H_{16}Cl_2O_3N_2S$ (M$^+$) 386.0258, found 386.0261.

Example 5

Preparation of rac-2-cyclopentyloxy-2-(3,4-dichloro-phenyl)-N-pyridin-2-yl-acetamide

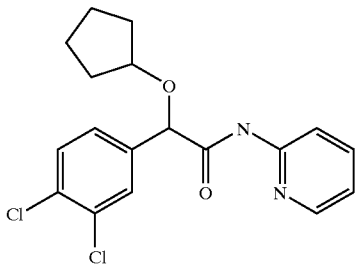

A solution of rac-cyclopentyloxy-(3,4-dichloro-phenyl)-acetic acid (from Example 1, 50 mg, 0.17 mmol) and triethylamine (0.07 mL, 0.52 mmol) in toluene (5 mL), previously cooled to 0° C. was treated with 2,4,6-trichlorobenzoyl chloride (0.03 mL, 0.19 mmol) and the mixture was stirred at 0° C. After 1 h, 2-aminopyridine (20 mg, 0.21 mmol) and 4-dimethylaminopyridine (5 mg, 0.035 mmol) were added and the stirring was continued for 1 h at 0° C. The reaction was checked for completion, then it was diluted with water (10 mL) and extracted with dichloromethane (3×10 mL). The combined organic extracts were dried over sodium sulfate, filtered and concentrated in vacuo. The product was purified by chromatography (Biotage Flash 12M column, 80/20 hexanes/ethyl acetate) to give rac-2-cyclopentyloxy-2-(3,4-dichloro-phenyl)-N-pyridin-2-yl-acetamide (48 mg, 76% yield) as a white foam: EI-HRMS m/e calculated for $C_{18}H_{18}N_2O_2Cl_2$ (M$^+$) 364.0745, found 364.0746.

Example 6

Preparation of rac-2-(3-chloro-4-methanesulfonyl-phenyl)-2-cyclopentyloxy-N-thiazol-2-yl-acetamide

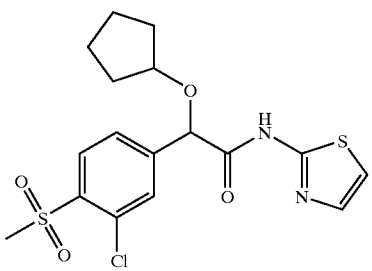

A solution of aluminum chloride (105.3 g, 789.4 mmol) in chloroform (300 mL), cooled to 0° C., was treated with methyl oxalyl chloride (46.52 mL, 505.8 mmol) in chloroform (300 mL) and the reaction was stirred at 0° C. After 30 min, the reaction was treated with a solution of 2-chlorothioanisole (75.00 g, 472.7 mmol) in chloroform (300 mL) and the stirred reaction was allowed to equilibrate to 25° C. After 4 h, the reaction mixture was poured slowly into ice (2 L) and allowed to sit for 15 min. It was then filtered through celite to remove the aluminum salts and the filtrate was extracted with dichloromethane (3×50 mL). The organic extracts were then washed with saturated sodium bicarbonate (1×1100 mL), dried over magnesium sulfate, filtered and evaporated under reduced pressure. The product, (3-chloro-4-methylsulfanyl-phenyl)-oxo-acetic acid methyl ester (39.22 g, 34% yield), which needed no further purification was isolated as a light yellow solid, mp 67.9–70.2° C.; EI-HRMS m/e calcd for $C_{10}H_9ClSO_3$ (M$^+$) 243.9961, found 243.9958.

To a clear solution of (3-chloro-4-methylsulfanyl-phenyl)-oxo-acetic acid methyl ester (5.00 g, 20.43 mmol) in methanol (100 mL) and water (10 mL) at 25° C. was added oxone (37.68 g, 61.29 mmol) in one portion and pH 4 phosphate buffer (5 mL). After the reaction was stirred for 5 h, it was concentrated in vacuo to remove methanol, then was diluted with water (50 mL) and was extracted with ethyl acetate (3×50 mL). The combined organic extracts were dried over magnesium sulfate, filtered and evaporated under reduced pressure. The product was purified by flash chromatography (Merck Silica gel 60, 230–400 mesh, 70/30 hexanes/ethyl acetate) to provide (3-chloro-4-methane-sulfonyl-phenyl)-oxo-acetic acid methyl (3.67 g, 65% yield) as a light yellow solid, mp 101.7–121.2° C.; EI-HRMS m/e calcd for $C_{10}H_9ClSO_5$ (M$^+$) 275.9859, found 275.9857.

A solution of (3-chloro-4-methanesulfonyl-phenyl)-oxo-acetic acid methyl ester (3.67 g, 13.26 mmol) and p-toluenesulfonylhydrazide (3.21 g, 17.24 mmol) in toluene (50 mL) was refluxed for 16 h in a flask fitted a Dean-Stark trap filled with 3 A molecular sieves. The reaction was then cooled to 25° C. and concentrated in vacuo. The residual material was flash chromatographed (Merck Silica gel 60, 230–400 mesh, 70/30 hexanes/ethyl acetate) to provide (3-chloro-4-methanesulfonyl-phenyl)-(4-toluene-sulfonylhydrazono)-acetic acid methyl ester (3.82 g, 65% yield) as an off white solid. The compound was used per se in the subsequent transformation.

A solution of (3-chloro-4-methanesulfonyl-phenyl)-(4-toluenesulfonyl-hydrazono)-acetic acid methyl ester (3.82 g, 8.5 mmol) and triethylamine (1.3 mL, 9.35 mmol) in dichloromethane (40 mL) was stirred at 25° C. After 1 h, the reaction was evaporated under reduced pressure and the resulting residue was purified by flash chromatography (Merck Silica gel 60, 230–400 mesh, 60/40 hexanes/ethyl acetate) to give (3-chloro-4-methanesulfonyl-phenyl)-diazo-acetic acid methyl ester (978 mg, 40% yield) as a bright yellowish orange solid, mp 102.7–106.5° C.; EI-HRMS m/e calcd for $C_{10}H_9N_2ClSO_4$ ($M^+$) 287.9972, found 287.9979.

A solution of (3-chloro-4-methanesulfonyl-phenyl)-diazo-acetic acid methyl ester (489 mg, 1.69 mmol) in dichloromethane (10 mL) at 25° C. was treated with cyclopentanol (0.38 mL, 4.23 mmol) followed by rhodium (II) acetate dimer (15 mg, 0.034 mmol). After the resulting solution was stirred at 25° C. for 1 h, it was diluted with dichloromethane (10 mL), poured into water (15 mL) and extracted with dichloromethane (3×10 mL). The combined organic extracts were dried over sodium sulfate, filtered and concentrated in vacuo. The product was purified by chromatography (Biotage Flash 40S column, 75/25 hexanes/ethyl acetate) to afford rac-(3-chloro-4-methanesulfonyl-phenyl)-cyclopentyloxy-acetic acid methyl ester (395 mg, 67% yield) as a colorless oil: EI-HRMS m/e calcd for $C_{15}H_{19}ClSO_5$ ($M^+$) 346.0642, found 346.0643.

A solution of rac-(3-chloro-4-methanesulfonyl-phenyl)-cyclopentyloxy-acetic acid methyl ester (395 mg, 1.14 mmol) in ethanol (15 mL) at 25° C. was treated with a solution of potassium hydroxide (320 mg, 5.69 mmol) in water (3 mL) and the mixture was stirred at 25° C. After 3 h, the reaction was diluted with water and evaporated under reduced pressure. The concentrate was acidified to pH 2 with an aqueous solution of 1N hydrochloric acid and extracted with dichloromethane (3×15 mL). The combined organic extracts were dried over sodium sulfate, filtered and evaporated in vacuo. The residual oil was purified by flash chromatography (Merck Silica gel 60, 230–400 mesh, 50/50 hexanes/ethyl acetate plus 1% acetic acid) to furnish rac-(3-chloro-4-methanesulfonyl-phenyl)-cyclopentyloxy-acetic acid (364 mg, 96% yield) as a colorless oil: EI-HRMS m/e calcd for $C_{14}H_{17}ClSO_5$ ($M^+$) 332.0485, found 332.0486.

To a stirred solution of rac-(3-chloro-4-methanesulfonyl-phenyl)-cyclopentyloxy-acetic acid (50 mg, 0.15 mmol) in dichloromethane (10 mL) at 25° C. was added 2-aminothiazole (23 mg, 0.23 mmol), BOP reagent (100 mg, 0.23 mmol) and triethylamine (0.06 mL, 0.45 mmol). The mixture was stirred at 25° C. for 16 h, then it was diluted with water (10 mL) and extracted with dichloromethane (3×20 mL). The combined organic layers were washed with water (1×10 mL), 1N sodium hydroxide (1×10 mL), 1N hydrochloric acid (1×10 mL) and brine (1×10 mL), then were dried over sodium sulfate, filtered and concentrated in vacuo. The product was purified by chromatography (Biotage Flash 40S column, 60/40 hexanes/ethyl acetate) to give rac-2-(3-chloro-4-methanesulfonyl-phenyl)-2-cyclopentyloxy-N-thiazol-2-yl-acetamide(44 mg, 71% yield) as a white solid: EI-HRMS m/e calculated for $C_{17}H_{19}N_2O_4S_2Cl$ ($M^+$) 414.0475, found 414.0481.

Example 7

Preparation of rac-1-[(3-chloro-4-methanesulfonyl-phenyl)-cyclopentyloxy-acetyl]-3-methyl-urea

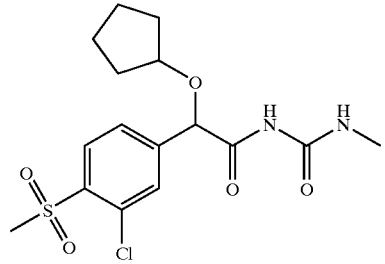

A cooled (0° C.) solution of rac-(3-chloro-4-methanesulfonyl-phenyl)-cyclopentyloxy-acetic acid (Example 6; 100 mg, 0.30 mmol) in fluorobenzene (2.5 mL) and N,N-dimethylformamide (1.8 μL). was treated with a 2.0 M solution of oxalyl chloride in dichloromethane (0.18 mL, 0.36 mmol). Immediately a vigorous gas evolution was observed, and the mixture was stirred at 25° C. for 1 h and became light yellow in color. Methyl urea (97 mg, 0.90 mmol) was then added and after the reaction was heated at 70° C. for 10 min, pyridine (0.048 mL, 0.60 mmol) was added and the reaction was maintained at 70° C. for 1 h. The cooled mixture was diluted with ethyl acetate (5 mL) then was filtered through Celite to remove insoluble materials and the filtrate concentrated in vacuo. The concentrate was washed with 3N hydrochloric acid (1×20 mL), saturated sodium bicarbonate (1×15 mL) and brine (1×15 mL), then was dried over sodium sulfate, filtered and evaporated under reduced pressure. The product was purified by chromatography (Biotage Flash 40S column, 50/50 hexanes/ethyl acetate) to provide rac-1-[(3-chloro-4-methanesulfonyl-phenyl)-cyclopentyloxy-acetyl]-3-methyl-urea (78 mg, 67% yield) as a white foam: FAB-HRMS m/e calculated for $C_{16}H_{21}N_2O_5SCl$ $(M+H)^+$ 389.0938, found 389.0943.

Example 8

Preparation of rac-2-(3-chloro-4-methanesulfonyl-phenyl)-2-(cyclohex-2-enyloxy)-N-thiazol-2-yl-acetamide

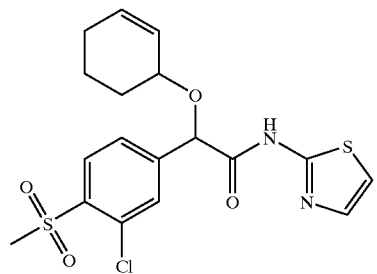

A solution of (3-chloro-4-methanesulfonyl-phenyl)-diazo-acetic acid methyl ester (Example 6; 489 mg, 1.69 mmol) in dichloromethane (10 ML) at 25° C. was treated with 2-cyclohexen-1-ol (0.42 mL, 4.23 mmol) followed by rhodium (II) acetate dimer (15 mg, 0.034 mmol) and the resulting solution was stirred at 25° C. for 1 h. The reaction mixture was diluted with dichloromethane (10 mL), then was poured into water (15 mL) and extracted with dichloromethane (3×10 mL). The combined organic layers were dried over sodium sulfate, filtered and concentrated in vacuo. The product was purified by chromatography (Biotage Flash 40S column, 75/25 hexanes/ethyl acetate) provided rac-(3-chloro-4-methanesulfonyl-phenyl)-(cyclohex-2-enyloxy)-acetic acid methyl ester (350 mg, 58% yield) as a colorless oil: EI-HRMS m/e calcd for $C_{16}H_{19}ClSO_5$ (M$^+$) 358.0642, found 358.0640.

A solution of rac-(3-chloro-4-methanesulfonyl-phenyl)-(cyclohex-2-enyloxy)-acetic acid methyl ester (350 mg, 0.98 mmol) in ethanol (15 mL) at 25° C. was treated with a solution of potassium hydroxide (273 mg, 4.88 mmol) in water (2.5 mL) and the solution was stirred at 25° C. After 3 h, the reaction was diluted with water and concentrated under reduced pressure. The concentrate was acidified to pH 2 with an aqueous solution of 1N hydrochloric acid and extracted with dichloromethane (3×15 mL). The combined organic layers were dried over sodium sulfate, filtered and evaporated under reduced pressure. The residual material was purified by flash chromatography (Merck Silica gel 60, 230–400 mesh, 50/50 hexanes/ethyl acetate plus 1% acetic acid) to give rac-(3-chloro-4-methanesulfonyl-phenyl)-(cyclohex-2-enyloxy)-acetic acid (265 mg, 79% yield) as a colorless oil: EI-HRMS m/e calcd for $C_{15}H_{17}ClSO_5$ (M$^+$) 344.0485, found 344.0494.

To a solution of rac-(3-chloro-4-methanesulfonyl-phenyl)-(cyclohex-2-enyloxy)-acetic acid (50 mg, 0.15 mmol) in dichloromethane (10 mL) at 25° C. was added 2-aminothiazole (22 mg, 0.22 mmol), BOP reagent (96.2 mg, 0.22 mmol) and triethylamine (0.06 mL, 0.44 mmol). The mixture was stirred at 25° C. for 16 h, then was diluted with water (10 mL) and extracted with dichloromethane (3×20 mL). The combined organic layers were washed with water (1×10 mL), 1N sodium hydroxide (1×10 mL), 1N hydrochloric acid (1×10 mL) and brine (1×10 mL), then were dried over sodium sulfate, filtered and evaporated under reduced pressure. The product was purified by chromatography (Biotage Flash 40S column, 60/40 hexanes/ethyl acetate) to furnish rac-2-(3-chloro-4-methanesulfonyl-phenyl)-2-(cyclohex-2-enyloxy)-N-thiazol-2-yl-acetamide (39 mg, 63% yield) as a glassy solid: EI-HRMS m/e calculated for $C_{18}H_{19}N_2O_4S_2Cl$ (M$^+$) 426.0475, found 426.0479.

Example 9

Preparation of rac-1-[(3-chloro-4-methanesulfonyl-phenyl)-(cyclohex-2-enyloxy)-acetyl]-3-methyl-urea

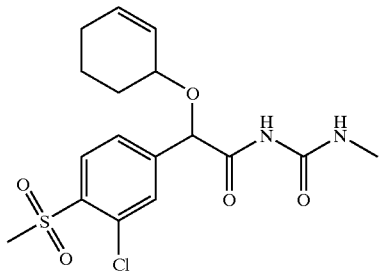

A cooled (0° C.) mixture of rac-(3-chloro-4-methanesulfonyl-phenyl)-(cyclohex-2-enyloxy)-acetic acid (from Example 8100 mg, 0.29 mmol), fluorobenzene (2.5 mL) and N,N-dimethylformamide (1.8 μL). was treated with a 2.0 M solution of oxalyl chloride in dichloromethane (0.18 mL, 0.36 mmol) which caused a vigorous evolution of gas. The reaction was then stirred at 25° C. for 1 h and became light yellow in color. After methyl urea (64 mg, 0.87 mmol) was added, the reaction was heated at 70° C. for 10 min, then pyridine (0.048 mL, 0.60 mmol) was added and the mixture was maintained at 70° C. for 1 h. The cooled reaction was diluted with ethyl acetate (5 mL), then was filtered through celite to remove insoluble materials and the filtrate was concentrated in vacuo. The concentrate was washed with 3N hydrochloric acid (1×20 mL), saturated sodium bicarbonate (1×15 mL), and brine (1×15 mL), then was dried over sodium sulfate, filtered and evaporated under reduced pressure. The reaction product was purified by chromatography (Biotage Flash 40S column, 50/50 hexanes/ethyl acetate) to give 1-[(3-chloro-4-methanesulfonyl-phenyl)-(cyclohex-2-enyloxy)-acetyl]-3-methyl-urea (63 mg, 54% yield) as a white foam: FAB-HRMS m/e calculated for $C_{17}H_{21}N_2O_5SCl$ (M+H)$^+$ 401.0938, found 401.0921.

Example 10

Preparation of rac-2-cyclopentylsulfanyl-2-(3,4-dichloro-phenyl)-N-thiazol-2-yl-acetamide

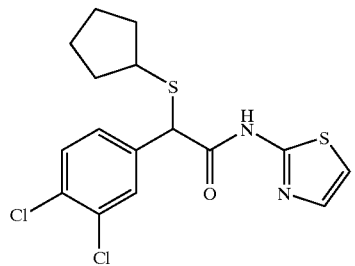

A solution of diazo-(3,4-dichloro-phenyl)-acetic acid methyl ester (Example 1; 193 mg, 0.79 mmol) in dichloromethane (10 mL) at 25° C. was treated with cyclopentyl mercaptan (0.21 mL, 1.97 mmol) followed by rhodium (II) acetate dimer (9 mg, 0.020 mmol) and the solution was stirred at 25° C. for 1 h. During this time no evolution of gas was detected, and examination of the black solution by thin layer chromatography indicated that only starting material was present. The reaction was heated to reflux and a second portion of rhodium (II) acetate dimer (10 mg, 0.024 mmol) was added and as the mixture was stirred at reflux for 110 min, a vigorous evolution of gas was observed. The reaction mixture was diluted with dichloromethane (10 mL), then was poured into water (15 mL) and extracted with dichloromethane (3×10 mL). The combined organic extracts were dried over sodium sulfate, filtered and evaporated under reduced pressure. The residual oil was purified by flash chromatography (Merck Silica gel 60, 230–400 mesh, 95/5 hexanes/ethyl acetate) to furnish rac-cyclopentylsulfanyl-(3,4-dichloro-phenyl)-acetic acid methyl ester (148 mg, 59% yield) as a colorless oil: EI-HRMS m/e calcd for $C_{14}H_{16}Cl_2SO_2$(M$^+$) 318.0248, found 318.0244.

A solution of rac-cyclopentylsulfanyl-(3,4-dichloro-phenyl)-acetic acid methyl ester (50 mg, 0.16 mmol) in ethanol (3 mL) at 25° C. was treated with a solution of potassium hydroxide (44 mg, 0.79 mmol) in water (1 mL) and the mixture was stirred at 25° C. After 3 h, the reaction was diluted with water and evaporated under reduced pressure. The concentrate was acidified to pH 2 with art aqueous solution of 1N hydrochloric acid and extracted with dichloromethane (3×15 mL). The combined organic extracts were dried over sodium sulfate, filtered and concentrated in vacuo. The residual material was purified by flash chromatography (Merck Silica gel 60, 230–400 mesh, 50/50 hexanes/ethyl acetate plus 1% acetic acid) to afford rac-cyclopentylsulfanyl-(3,4-dichloro-phenyl)-acetic acid (43 mg, 90% yield) as a colorless oil: EI-HRMS m/e calcd for $C_{13}H_{14}Cl_2SO_2$ ($M^+$) 304.0091, found 304.0101.

Cyclopentylsulfanyl-(3,4-dichloro-phenyl)-acetic (43 mg, 0.14 mmol) was dissolved in dichloromethane (10 mL) and to this solution at 25° C. was added 2-aminothiazole (21 mg, 0.21 mmol), BOP reagent (92 mg, 0.21 mmol) and triethylamine (0.06 mL, 0.42 mmol). The reaction mixture was stirred at 25° C. for 16 h, then was diluted with water (10 mL) and extracted with dichloromethane (3×15 mL). The combined organic layers were washed with water (1×10 mL), 1N sodium hydroxide (1×10 mL), 1N hydrochloric acid (1×10 mL) and brine (1×10 mL), then were dried over sodium sulfate, filtered and evaporated under reduced pressure. The product was purified by chromatography (Biotage Flash 12M column, 80/20 hexanes/ethyl acetate) to furnish rac-2-cyclopentylsulfanyl-2-(3,4-dichloro-phenyl)-N-thiazol-2-yl-acetamide (40 mg, 74% yield) as a colorless oil: EI-HRMS m/e calculated for $C_{16}H_{16}N_2OS_2Cl_2$ ($M^+$) 386.0081, found 386.0080.

Example 11

Preparation of rac-2-cyclopentanesulfonyl-2-(3,4-dichloro-phenyl)-N-thiazol-2-yl-acetamide

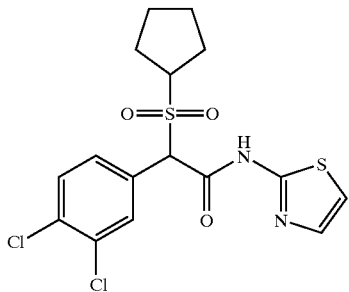

To a solution of rac-2-cyclopentylsulfanyl-2-(3,4-dichloro-phenyl)-N-thiazol-2-yl-acetamide (Example 10; 34 mg, 0.088 mmol) in methanol (2 mL) was added a solution of sodium periodate (34 mg, 0.16 mmol) in water (1 mL) and the mixture was stirred at 25° C. After 6 h, the precipitate was filtered off and washed with dichloromethane (15 mL). The organic layer was set aside and the aqueous layer was extracted with dichloromethane (3×10 mL). The combined organic layers were dried over sodium sulfate, filtered and evaporated under reduced pressure. Chromatography of the residue (Biotage Flash 12M column, 50/50 hexanes/ethyl acetate) afforded rac-2-cyclopentanesulfinyl-2-(3,4-dichloro-phenyl)-N-thiazol-2-yl-acetamide (23 mg, 66% yield) as a colorless oil: EI-HRMS m/e calculated for $C_{16}H_{16}N_2O_2S_2Cl_2$ ($M^+$) 402.0030, found 402.0035.

A solution of rac-2-cyclopentanesulfinyl-2-(3,4-dichloro-phenyl)-N-thiazol-2-yl-acetamide (20 mg, 0.05 mmol) in methanol (2 mL) was stirred at 25° C. as a solution of potassium permanganate (9 mg, 0.06 mmol) in water (0.5 mL) was added. The mixture was stirred at 25° C. for 30 min and then was filtered. The filter cake was washed with dichloromethane and the combined filtrates were washed with sodium bicarbonate solution (10 mL) and brine (10 mL), then were dried over sodium sulfate, filtered and concentrated in vacuo. The product was purified by chromatography (Biotage Flash 12M column, 50/50 hexanes/ethyl acetate) to provide rac-2-cyclopentanesulfonyl-2-(3,4-dichloro-phenyl)-N-thiazol-2-yl-acetamide(10 mg, 48% yield) as a colorless oil: EI-HRMS m/e calculated for $C_{16}H_{16}N_2O_3S_2Cl_2$ ($M^+$) 417.9979, found 417.9977.

Example 12

Preparation of rac-1-[cyclopentyloxy-(3,4-dichloro-phenyl)-acetyl]-3-methyl-urea

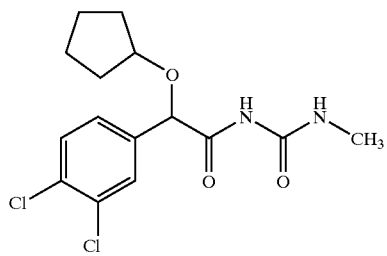

A cooled (0° C.) solution of rac-cyclopentyloxy-(3,4-dichloro-phenyl)-acetic acid (Example 1; 164 mg, 0.57 mmol) in dichloromethane (10 mL) and N,N-dimethylformamide (one drop) was treated with oxalyl chloride (2.0 M solution in dichloromethane, 0.43 mL, 0.86 mmol). The reaction was stirred at 0° C. for 1 h, then 1,1,1,3,3,3-hexamethyldisilazane (0.42 mL, 2.0 mmol) was added and the resulting cloudy mixture was stirred at 25° C. for 16 h. The reaction was quenched with methanol (10 mL), washed with an aqueous solution of 5% sulfuric acid (2×15 mL) and extracted with dichloromethane (3×10 mL). The combined organic extracts were washed with brine (1×10 mL), then were dried over magnesium sulfate, filtered and concentrated in vacuo. The residue was purified by flash chromatography (Merck Silica gel 60, 230–400 mesh, 60/40 hexanes/ethyl acetate) to give rac-2-cyclopentyloxy-2-(3,4-dichloro-phenyl)-acetamide (116 mg, 71% yield) as a white solid, mp 88.3–91.4° C.; FAB-HRMS m/e calcd for $C_{13}H_{15}NCl_2O_2$ ($M^+$) 288.0558, found 288.0572.

A solution of rac-2-cyclopentyloxy-2-(3,4-dichloro-phenyl)-acetamide (116 mg, 0.40 mmol) in toluene (5 mL) was treated with methyl isocyanate (0.04 mL, 0.60 mmol). The resulting solution was heated to reflux for 24 h, then was cooled and was evaporated under reduced pressure. The resulting oil was purified by flash chromatography (Merck Silica gel 60, 230–400 mesh, 60/40 hexanes/ethyl acetate) to furnish 1-[cyclopentyloxy-(3,4-dichloro-phenyl)-acetyl]-3-methyl-urea (30 mg, 41% yield) as a colorless oil: EI-HRMS m/e calcd for $C_{15}H_{18}N_2Cl_2O_3$ ($M^+$) 288.0558, found 288.0572.

Example 13

Preparation of rac-1-[(cyclohex-2-enyloxy)-(3,4-dichloro-phenyl)-acetyl]-3-methyl-urea

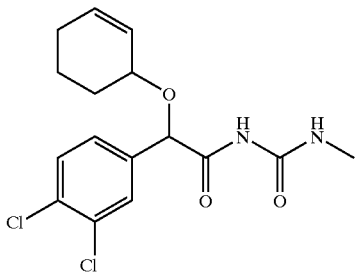

A solution of rac-(cyclohex-2-enyloxy)-(3,4-dichloro-phenyl)-acetic acid (Example 3; 409 mg, 1.36 mmol) in dichloromethane (10 mL) and N,N-dimethylformamide (one drop) cooled to 0° C. was treated with oxalyl chloride (2.0 M solution in dichloromethane, 0.95 mL, 1.90 mmol). The reaction was stirred at 0° C. for 1 h, then 1,1,1,3,3,3-hexamethyldisilazane (1.0 mL, 4.75 mmol) was added and the resulting cloudy mixture was stirred at 25° C. for 16 h. The reaction was quenched with methanol (10 mL), washed with an aqueous solution of 5% sulfuric acid (2×15 mL) and extracted with dichloromethane (3×10 mL). The combined organic extracts were washed with brine (1×10 mL), dried over magnesium sulfate, filtered and concentrated in vacuo. The reaction product was purified by flash chromatography (Merck Silica gel 60, 230–400 mesh, 70/30 hexanes/ethyl acetate) to give rac-2-(cyclohex-2-enyloxy)-2-(3,4-dichloro-phenyl)-acetamide (311 mg, 76% yield) as a white solid: 103.6–108.9° C.; EI-HRMS m/e calcd for $C_{14}H_{15}NCl_2O_2$ (M+) 299.0479, found 299.0492.

A solution of rac-2-(cyclohex-2-enyloxy)-2-(3,4-dichloro-phenyl)-acetamide (311 mg, 1.04 mmol) in toluene (10 mL) was treated with methyl isocyanate (0.09 mL, 1.55 mmol). The resulting solution was heated at reflux for 24 h and then was concentrated in vacuo. The residual material was purified by flash chromatography (Merck Silica gel 60, 230–400 mesh, 90/10 hexanes/ethyl acetate) to furnish 1-[(cyclohex-2-enyloxy)-(3,4-dichloro-phenyl)-acetyl] h-3-methyl-urea (238 mg, 64% yield) as a colorless oil: EI-HRMS m/e calcd for $C_{16}H_{18}N_2Cl_2O_3$ (M+) 356.0694, found 356.0694.

Example 14

Preparation of rac-1-[cyclohexyloxy-(3,4-dichloro-phenyl)-acetyl]-3-methyl-urea

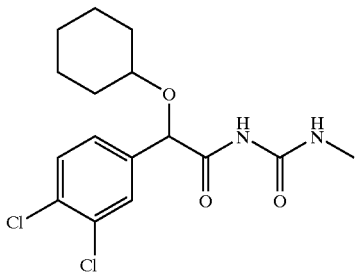

A solution of rac-cyclohexyloxy-(3,4-dichloro-phenyl)-acetic acid (Example 2; 364 mg, 1.20 mmol) in dichloromethane (10 mL) and N,N-dimethylformamide (one drop) cooled to 0° C. was treated with oxalyl chloride (2.0M solution in dichloromethane, 0.84 mL, 1.68 mmol). The reaction was stirred at 0° C. for 1 h, then 1,1,1,3,3,3-hexamethyldisilazane (0.90 mL, 4.20 mmol) was added and the cloudy mixture was stirred at 25° C. for 16 h. At this time, the reaction was quenched with methanol (10 mL), washed with an aqueous solution of 5% sulfuric acid (2×15 mL) and extracted with dichloromethane (3×10 mL). The combined organic extracts were washed with brine (1×10 mL), then were dried over magnesium sulfate, filtered and evaporated under reduced pressure. The product was purified by flash chromatography (Merck Silica gel 60, 230–400 mesh, 90/10 hexanes/ethyl acetate) to afford rac-2-cyclohexyloxy-2-(3,4-dichloro-phenyl)-acetamide (311 mg, 76% yield) as a colorless oil: FAB-HRMS m/e calcd for $C_{14}H_{17}NCl_2O_2$ (M+H)+ 302.0714, found 302.0728.

A solution of rac-2-cyclohexyloxy-2-(3,4-dichloro-phenyl)-acetamide (291 mg, 0.96 mmol) in toluene (10 mL) was treated with methyl isocyanate (0.09 mL, 1.44 mmol). The resulting solution was heated at reflux for 24 h and then the cooled reaction was concentrated in vacuo. The reaction product was purified by flash chromatography (Merck Silica gel 60, 230–400 mesh, 90/10 hexanes/ethyl acetate) to give 1-[cyclohexyloxy-(3,4-dichloro-phenyl)-acetyl]-3-methyl-urea (301 mg, 87% yield) as a colorless oil: EI-HRMS m/e calcd for $C_{16}H_{20}N_2Cl_2O_3$ (M+H)+ 359.0929, found 359.0922.

Example 15

Preparation of rac-[1-[(3,4-dichloro-phenyl)-(tetrahydro)-pyran-4-yloxy)-acetyl]-3-methyl-urea

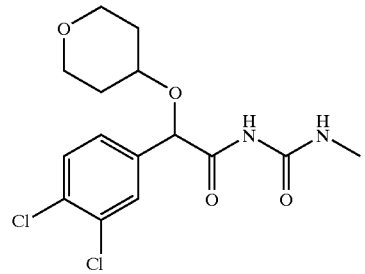

A cooled (0° C.) solution of rac-(3,4-dichloro-phenyl)-[(tetrahydro-pyran-4-yloxy)]-acetic acid (Example 4; 441 mg, 1.45 mmol) in dichloromethane (10 mL) and N,N-dimethylformamide (one drop) was treated with oxalyl chloride (2.0 M solution in dichloromethane, 1.01 mL, 2.02 mmol). The reaction was stirred at 0° C. for 1 h, then 1,1,1,3,3,3-hexamethyldisilazane (1.10 mL, 5.06 mmol) was added and the resulting cloudy mixture was stirred at 25° C. for 16 h. The reaction was quenched with methanol (10 mL), washed with an aqueous solution of 5% sulfuric acid (2×15 mL) and extracted with dichloromethane (3×10 mL). The combined organic extracts were washed with brine (1×10 mL), then were dried over magnesium sulfate, filtered and evaporated under reduced pressure. The resulting residue was purified by flash chromatography (Merck Silica gel 60, 230–400 mesh, 70/30 hexanes/ethyl acetate) to provide rac-2-(3,4-dichloro-phenyl)-2-(tetrahydro-pyran-4-yloxy)-acetamide (278 mg, 63% yield) as a white solid, mp 81.9–83.6° C.; FAB-HRMS m/e calcd for $C_{13}H_{15}NCl_2O_3$ (M+H)+ 303.0428, found 303.0426.

A solution of rac-2-(3,4-dichloro-phenyl)-2-(tetrahydro-pyran-4-yloxy)-acetamide (278 mg, 0.91 mmol) in toluene (10 mL) was treated with methyl isocyanate (0.08 mL, 1.37 mmol). The resulting solution was heated at reflux for 24 h and then the cooled reaction was concentrated in vacuo. The resulting oil was purified by flash chromatography (Merck Silica gel 60, 230–400 mesh, 20/80 hexanes/ethyl acetate) to afford [1[(3,4-dichloro-phenyl)-(tetrahydro-pyran-4-yloxy)-acetyl]-3-methyl-urea (70 mg, 21% yield) as a colorless oil: EI-HRMS m/e calcd for $C_{15}H_{18}N_2Cl_2O_4$ ($M^+$) 360.0643, found 360.0865.

Example 16

Preparation of rac-3-cyclopentyl-2-(3,4-dichloro-phenyl)-3-oxo-N-thiazol-2-yl-propionamide

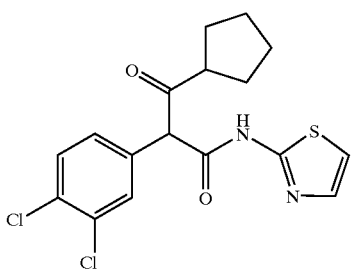

To a solution of (3,4-dichloro-phenyl)-acetic acid (500 mg, 2.4 mmol) in N,N-dimethylformamide (15 mL) at 25° C. was added HBTU (1.02 g, 2.7 mmol), 2-aminothiazole (360 mg, 3.6 mmol) and diisopropylethylamine (1.25 mL, 7.2 mmol). The reaction mixture was stirred for 16 h, then was diluted with water (10 mL) and extracted with ethyl acetate (3×15 mL). The combined organic layers were washed in turn with water (1×10 mL), 1N sodium hydroxide (1×10 mL), 1 N hydrochloric acid (1×10 mL) and brine (1×10 mL), then were dried over sodium sulfate, filtered and evaporated under reduced pressure. The residual material was purified by flash chromatography (Merck Silica gel 60, 230–400 mesh, 50150 hexanes/ethyl acetate) to furnish rac-2-(3,4-dichloro-phenyl)-N-thiazol-2-yl-acetamide (480 mg, 70% yield) as a light yellow solid, mp 169.8–172.3° C. EI-HRMS m/e calcd for $C_{11}H_8N_2OSCl_2$ ($M^+$) 285.9734, found 285.9734.

To a solution of rac-2-(3,4-dichloro-phenyl)-N-thiazol-2-yl-acetamide (185 mg, 0.64 mmol) in tetrahydrofuran (15 mL), previously cooled to −78° C., was added slowly a 1.0 M solution of lithium bis(trimethylsilyl)amide (1.3 mL, 1.3 mmol). The solution was stirred for 15 min at −78° C., then cyclopentanecarbonyl chloride (0.08 mL, 0.64 mmol) was dropwise added. The reaction mixture was stirred for an additional 60 min at −78° C. before it was quenched by the addition of a saturated ammonium chloride solution (10 mL). The mixture was then extracted with ethyl acetate (3×10 mL), dried over sodium sulfate, filtered and concentrated in vacuo. The product was purified by flash chromatography (Merck Silica gel 60, 230–400 mesh, 80/20 hexanes/ethyl acetate) to afford 3-cyclopentyl-2-(3,4-dichloro-phenyl)-3-oxo-N-thiazol-2-yl-propionamide (98 mg, 40% yield) as a yellow-orange solid: EI-HRMS m/e calcd for $C_{17}H_{16}N_2O_2SCl_2$ ($M^+$) 382.0309, found 382.0309.

Biological Activity Examples
a) In Vitro Glucokinase Activity

Glucokinase Assay: Glucokinase (GK) was assayed by coupling the production of glucose-6-phosphate to the generation of NADH with glucose-6-phosphate dehydrogenase (G6PDH, 0.75–1 kunits/mg; Boehringer Mannheim, Indianapolis, Ind.) from *Leuconostoc mesenteroides* as the coupling enzyme (Scheme 2). Recombinant Scheme 2

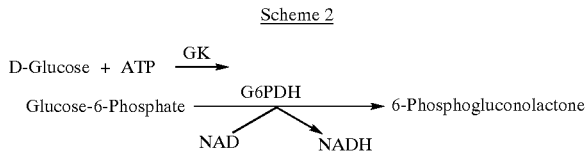

Human liver GK1 was expressed in *E. coli* as a glutalhione S-transferase fusion protein (GST-GK) [Liang et al, 1995] and was purified by chromatography over a glutathione-Sepharose 4B affinity column using the procedure provided by the manufacturer (Amersham Pharmacia Biotech, Piscataway, N.J.). Previous studies have demonstrated that the enzymatic properties of native GK and GST-GK are essentially identical (Liang et al, 1995; Neet et al., 1990).

The assay was conducted at 25° C. in a flat bottom 96-well tissue culture plate from Costar (Cambridge, Mass.) with a final incubation volume of 120 μL. The incubation mixture contained: 25 mM Hepes buffer (pH, 7.1), 25 mM KCl, 5 mM D-glucose, 1 mM ATP, 1.8 mM NAD, 2 mM $MgCl_2$, 1 μM sorbitol-6-phosphate, 1 mM dithiothreitol, test drug or 10% DMSO, 1.8 unit/ml G6PDH, and GK (see below). All organic reagents were >98% pure and were from Boehringer Mannheim with the exceptions of D-glucose and Hepes that were from Sigma Chemical Co, St Louis, Mo. Test compounds were dissolved in DMSO and were added to the incubation mixture minus GST-GK in a volume of 12 μl to yield a final DMSO concentration of 10%. This mix was preincubated in the temperature controlled chamber of a SPECTRAmax 250 microplate spectrophotometer (Molecular Devices Corporation, Sunnyvale, Calif.) for 10 minutes to allow temperature equilibrium and then the reaction was started by the addition of 20 μl GST-GK.

After addition of enzyme, the increase in optical density (OD) at 340 nm was monitored over a 10 minute incubation period as a measure of GK activity. Sufficient GST-GK was added to produce an increase in $OD_{340}$ of 0.08 to 0.1 units over the 10 minute incubation period in wells containing 10% DMSO, but no test compound. Preliminary experiments established that the GK reaction was linear over this period of time even in the presence of activators that produced a 5-fold increase in GK activity. The GK activity in control wells was compared with the activity in wells containing test GK activators, and the concentration of activator that produced a 50% increase in the activity of GK, i.e., the $SC_{1.5}$, was calculated. All of the compounds of formula I described in the Synthesis Examples had an $SC_{1.5}$ less than or equal to 30 μM.

Liang, Y., Kesavan, P., Wang, L., Niswender, K., Tanizawa, Y., Permut, M. A., Magnuson, M., and Matschinsky, F. M. Variable effects of maturity-onset-diabetes-of-youth (MODY)-associated glucokinase mutations on the substrate interactions and stability of the enzyme. *Biochem. J* 309: 167–173, 1995.

Neet, K., Keenan, R. P., and Tippett, P. S. Observation of a kinetic slow transition in monomeric glucokinase. *Biochemistry* 29;770–777, 1990.
b) In vivo Activity
Glucokinase Activator in vivo Screen Protocol C57BL/6J mice are orally dosed via gavage with Glucokinase (GK) activator at 50 mg/kg body weight following a two hour fasting period. Blood glucose determinations are made five times during the six hour post-dose study period.

Mice (n=6) are weighed and fasted for a two hour period prior to oral treatment. GK activators are formulated at 6.76 mg/ml in Gelucire vehicle (Ethanol:Gelucire44/14:PEG400q.s. 4:66:30 v/w/v. Mice are dosed orally with 7.5 µL formulation per gram of body weight to equal a 50 mg/kg dose. Immediately prior to dosing, a pre dose (time zero) blood glucose reading is acquired by snipping off a small portion of the animals tail (~1 mm) and collecting 15 µL blood into a heparinized capillary tube for analysis. Following GK activator administration, additional blood glucose readings are taken at 1, 2, 4, and 6 hours post dose from the same tail wound. Results are interpreted by comparing the mean blood glucose values of six vehicle treated mice with six GK activator treated mice over the six hour study duration. Compounds are considered active when they exhibit a statistically significant (p≦0.05) decrease in blood glucose compared to vehicle for two consecutive assay time points.

Example A

Tablets containing the following ingredients can be produced in a conventional manner:

| Ingredients | mg per tablet |
| --- | --- |
| Compound of formula (I) | 10.0–100.0 |
| Lactose | 125.0 |
| Corn starch | 75.0 |
| Talc | 4.0 |
| Magnesium stearate | 1.0 |

Example B

Capsules containing the following ingredients can be produced in a conventional manner:

| Ingredients | mg per capsule |
| --- | --- |
| Compound of formula (I) | 25.0 |
| Lactose | 150.0 |
| Corn starch | 20.0 |
| Talc | 5.0 |

Upon reading the present specification, various alternative embodiments will become obvious to the skilled artisan. These variations are to be considered within the scope and spirit of the subject invention which is only to be limited by the claims that follow and their equivalents.

What is claimed is:

1. A compound of the formula:

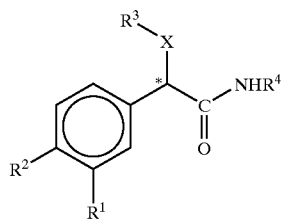

I wherein $R^1$ and $R^2$ are independently hydrogen, halo, cyano, nitro, lower alkylthio, perfluoro loweralkylthio, lower alkyl sulfonyl, or perfluoro-lower alkyl sulfonyl;

$R^3$ is lower alkyl having from 2 to 4 carbon atoms or a 5 to 7-membered ring which is cycloalkyl, cycloalkenyl, or heterocycloalkyl having one heteroatom selected from oxygen and sulfur;

$R^4$ is —C(O)NHR$^5$;

$R^5$ is hydrogen, lower alkyl, lower alkenyl, hydroxy lower alkyl, halo lower alkyl, —(CH$_2$)$_n$—C(O)—OR$^7$, —C(O)—(CH$_2$)$_n$—C(O)—OR$^8$;

$R^7$ and $R^8$ are independently hydrogen or lower alkyl;

X is oxygen, sulfur, sulfonyl or carbonyl; and the * indicates an asymmetric carbon atom;

or a pharmaceutically acceptable salt thereof.

2. The compound of claim 1, wherein said compound is of the formula:

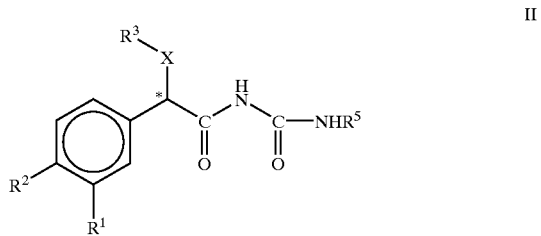

II wherein $R^1$ and $R^2$ are independently hydrogen, halo, lower alkyl sulfonyl, or perfluoro-lower alkyl sulfonyl;

$R^3$ is a 5 to 7-membered ring which is cycloalkyl, cycloalkenyl, or heterocycloalkyl having one heteroatom selected from oxygen and sulfur;

$R^5$ is lower alkyl;

X is oxygen, sulfur, sulfonyl or carbonyl; and the * indicates an asymmetric carbon atom, or a pharmaceutically acceptable salt thereof.

3. The compound of claim 2, wherein $R^1$ and $R^2$ are independently halo or lower alkyl sulfonyl and $R^3$ is a 5 to 7-membered ring which is cyclopentyl, cyclohexyl, cyclohexenyl, or a six-membered heterocycloalkyl having one heteroatom selected from oxygen and sulfur.

4. The compound of claim 3, wherein the heteroatom is oxygen.

5. The compound of claim 4, wherein $R^5$ is methyl.

6. The compound of claim 5, where X is oxygen.

7. The compound of claim 6, wherein $R^1$ and $R^2$ are independently chloro or methyl sulfonyl.

8. The compound of claim 7, wherein $R^1$ and $R^2$ are chloro.

9. The compound of claim 8 which is 1-[cyclopentyloxy-(3,4-dichloro-phenyl)-acetyl]-3-methyl-urea.

10. The compound of claim 8 which is 1-[cyclohexyloxy-(3,4-dichloro-phenyl)-acetyl]-3-methyl-urea.

11. The compound of claim 8 which is 1-[(cyclohex-2-enyloxy)-(3,4-dichloro-phenyl)-acetyl]-3-methyl-urea.

12. The compound of claim 8 which is [1-[(3,4-dichloro-phenyl)-(tetrahydro-pyran-4-yloxy)-acetyl]-3-methyl-urea.

13. The compound of claim 7, wherein $R^1$ is chloro and $R^2$ is methyl sulfonyl.

14. The compound of claim 13 which is 1-[(3-chloro-4-methanesulfonyl-phenyl)-cyclopentyloxy-acetyl]-3-methyl-urea.

15. The compound of claim 13 which is 1-[(3-chloro-4-methanesulfonyl-phenyl)-(cyclohex-2-enyloxy)-acetyl]-3-methyl-urea.

* * * * *